United States Patent
Wingeier et al.

(10) Patent No.: US 10,315,026 B2
(45) Date of Patent: Jun. 11, 2019

(54) ELECTRODE POSITIONING SYSTEM AND METHOD

(71) Applicant: Halo Neuro, Inc., San Francisco, CA (US)

(72) Inventors: Brett Wingeier, San Francisco, CA (US); Tal Bar-Or, San Francisco, CA (US); Colin Davis, San Francisco, CA (US); Victoria Hammett, San Francisco, CA (US); Daniel Chao, San Francisco, CA (US); Matty Martin, San Francisco, CA (US)

(73) Assignee: Halo Neuro, Inc., San Francisco, CA (US)

( * ) Notice: Subject to any disclaimer, the term of this patent is extended or adjusted under 35 U.S.C. 154(b) by 280 days.

(21) Appl. No.: 15/335,240

(22) Filed: Oct. 26, 2016

(65) Prior Publication Data
US 2017/0113033 A1    Apr. 27, 2017

Related U.S. Application Data

(60) Provisional application No. 62/236,200, filed on Oct. 26, 2015, provisional application No. 62/289,709, filed on Feb. 1, 2016.

(51) Int. Cl.
*A61N 1/04* (2006.01)
*A61N 1/36* (2006.01)
*A61B 5/00* (2006.01)
*H04R 5/033* (2006.01)

(52) U.S. Cl.
CPC .......... *A61N 1/0476* (2013.01); *A61B 5/6803* (2013.01); *A61B 5/6814* (2013.01); *A61N 1/0456* (2013.01); *A61N 1/36025* (2013.01); *A61N 1/0492* (2013.01); *H04R 5/033* (2013.01); *H04R 5/0335* (2013.01); *H04R 2460/13* (2013.01)

(58) Field of Classification Search
CPC ... A61B 5/0476; A61B 5/0478; A61B 5/6803; A61B 5/6814; A61B 5/6815; A61B 5/6831; A61B 5/6835; A61B 5/6898; A61N 1/0484; A61N 2005/0645; A61N 2005/0647
See application file for complete search history.

(56) References Cited

U.S. PATENT DOCUMENTS

| | | |
|---|---|---|
| 4,928,696 A | 5/1990 | Henderson et al. |
| 5,087,242 A | 2/1992 | Petelenz et al. |
| 5,622,168 A | 4/1997 | Keusch et al. |

(Continued)

*Primary Examiner* — Eugene T Wu
(74) *Attorney, Agent, or Firm* — Jeffrey Schox

(57) ABSTRACT

A system and method for stimulating a user, the system comprising: a set of pads configured at head regions of the user; a band having a first end coupled to a first pad of the set of pads and a second end coupled to a second pad of the set of pads; a bridge coupled the band and to an electrode during use; and a set of links, each link coupled at a first region to an interior portion of its corresponding pad, and coupled at a second region to the bridge, having an elastic modulus above a threshold modulus such that: in a first mode, displacement of the set of pads produces displacement of the electrode away from the head region of the user, and in a second mode, release of the set of pads orients protrusions of the electrode approximately normal to the head region.

18 Claims, 16 Drawing Sheets

(56) References Cited

U.S. PATENT DOCUMENTS

| | | |
|---|---|---|
| 6,077,237 A | 6/2000 | Campbell et al. |
| 6,406,811 B1* | 6/2002 | Hall .................... H04R 1/1025 |
| | | 429/96 |
| 7,828,947 B2 | 11/2010 | Oki et al. |
| 7,988,917 B2 | 8/2011 | Roesicke et al. |
| 8,795,174 B2 | 8/2014 | Manicka et al. |
| 8,838,247 B2 | 9/2014 | Hagedorn et al. |
| 9,486,618 B2 | 11/2016 | Wingeier et al. |
| 9,630,005 B2 | 4/2017 | Wingeier et al. |
| 9,643,001 B2 | 5/2017 | Wu et al. |
| 9,731,127 B2 | 8/2017 | Kealey et al. |
| 9,913,973 B2 | 3/2018 | Yanaki |
| 2005/0165460 A1 | 7/2005 | Efran |
| 2006/0229502 A1 | 10/2006 | Pollock et al. |
| 2007/0093706 A1 | 4/2007 | Gevins et al. |
| 2007/0238945 A1 | 10/2007 | Delic et al. |
| 2008/0021520 A1 | 1/2008 | Dietrich |
| 2010/0030129 A1 | 2/2010 | Nitzan et al. |
| 2011/0288610 A1 | 11/2011 | Brocke |
| 2011/0319975 A1 | 12/2011 | Ho et al. |
| 2012/0184894 A1 | 7/2012 | Imran et al. |
| 2012/0226127 A1* | 9/2012 | Asjes ................. A61B 5/04085 |
| | | 600/383 |
| 2012/0289869 A1 | 11/2012 | Tyler |
| 2013/0281759 A1 | 10/2013 | Hagedorn et al. |
| 2014/0148872 A1 | 5/2014 | Goldwasser et al. |
| 2014/0277324 A1 | 9/2014 | DiUbaldi et al. |
| 2014/0350431 A1* | 11/2014 | Hagedorn ............ A61B 5/0478 |
| | | 600/544 |
| 2015/0374971 A1 | 12/2015 | Dar et al. |
| 2015/0375007 A1* | 12/2015 | Takeuchi ............. A61N 5/0617 |
| | | 607/90 |
| 2016/0346530 A1 | 12/2016 | Jeffery et al. |
| 2016/0360990 A1* | 12/2016 | Altshuler ............ A61B 5/0478 |
| 2016/0366507 A1* | 12/2016 | Hou .................... H04R 1/1041 |
| 2017/0021158 A1 | 1/2017 | Wingeier et al. |
| 2017/0224978 A1 | 8/2017 | Lee |
| 2017/0224990 A1 | 8/2017 | Goldwasser et al. |
| 2017/0368344 A1 | 12/2017 | Ironi et al. |
| 2018/0021565 A1 | 1/2018 | Dar et al. |

* cited by examiner

ELECTRODE POSITIONING SYSTEM AND METHOD

CROSS-REFERENCE TO RELATED APPLICATIONS

This application claims the benefit of U.S. Provisional Application Ser. No. 62/236,200 filed 26 Oct. 2015 and U.S. Provisional Application Ser. No. 62/289,709 filed 1 Feb. 2016, which are each incorporated in their entirety herein by this reference.

TECHNICAL FIELD

This invention relates generally to the biosignals field, and more specifically to a new and useful electrode positioning system and method.

BACKGROUND

Electrode systems in the biosignals field are used to transmit electrical signals to a subject, and can be used to detect or measure biosignals from the subject. Current electrode systems for electrical stimulation and/or biosignal detection are, however, insufficient for many reasons including inadequate contact between the subject and the electrode(s) of a system, non-robust contact between the subject and the electrode(s) of a system, inadequate accommodation of individual anatomical variation across subjects, subject discomfort while using an electrode system, and/or limited use within multiple electrical simulation or biosignal detection paradigms. Furthermore, current systems and methods generally fail to allow a user to properly position electrodes at a head region by him/herself in a non-clinical or non-research environment.

Thus, there is a need in the biosignals field for a new and useful electrode positioning system and method. This invention provides such a new and useful system and method.

DESCRIPTION OF THE PREFERRED EMBODIMENTS

Figure 1:
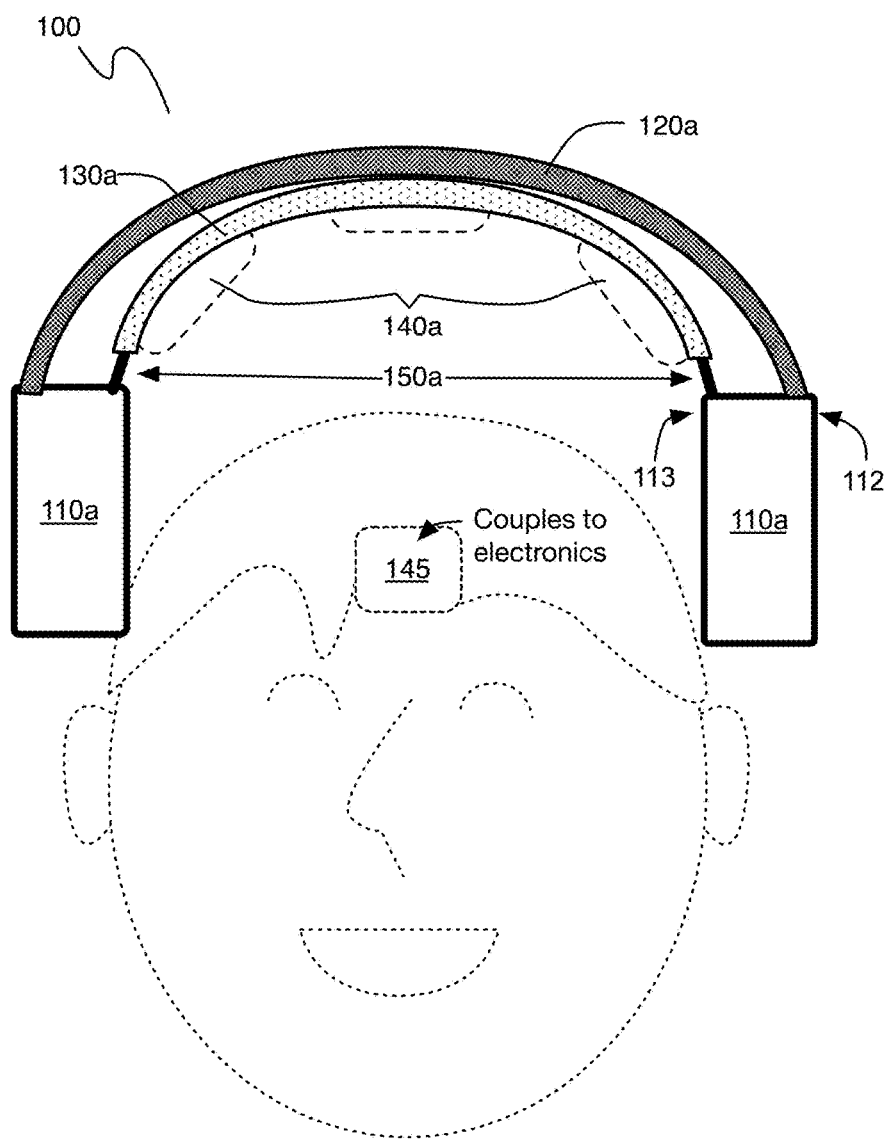
FIG. 1 depicts a schematic of an embodiment of an electrode positioning system.
Figure 2A:
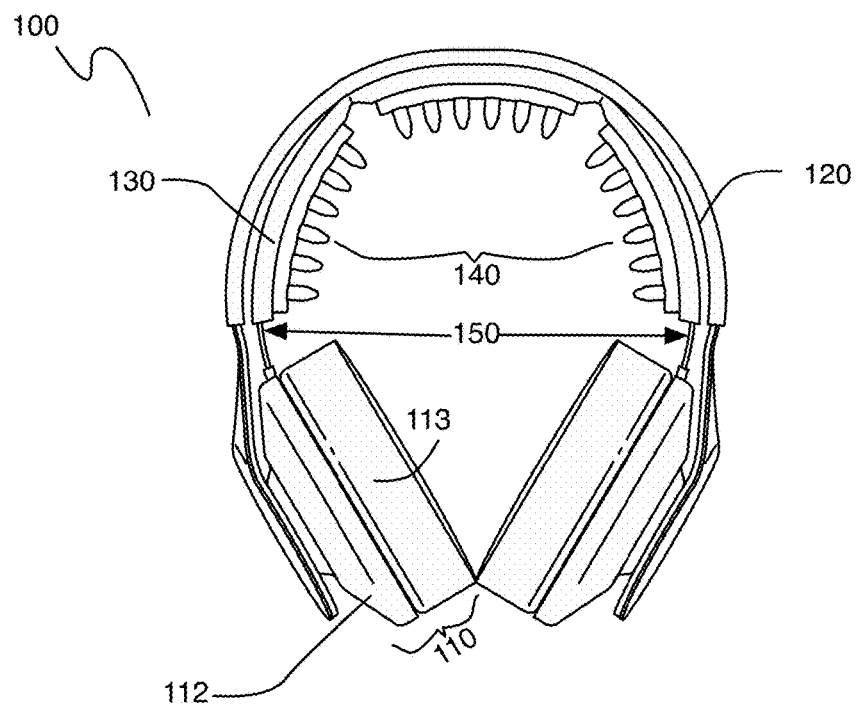
FIGS. 2A-2D depict a first specific example of an embodiment of an electrode positioning system.
Figure 2B:
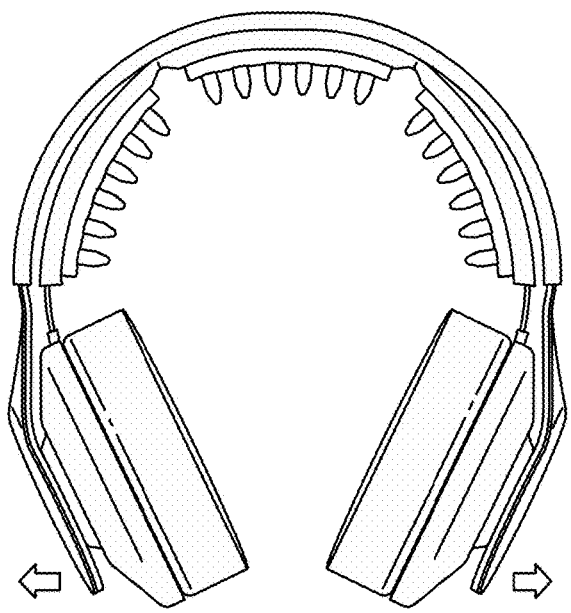
Figure 2C:
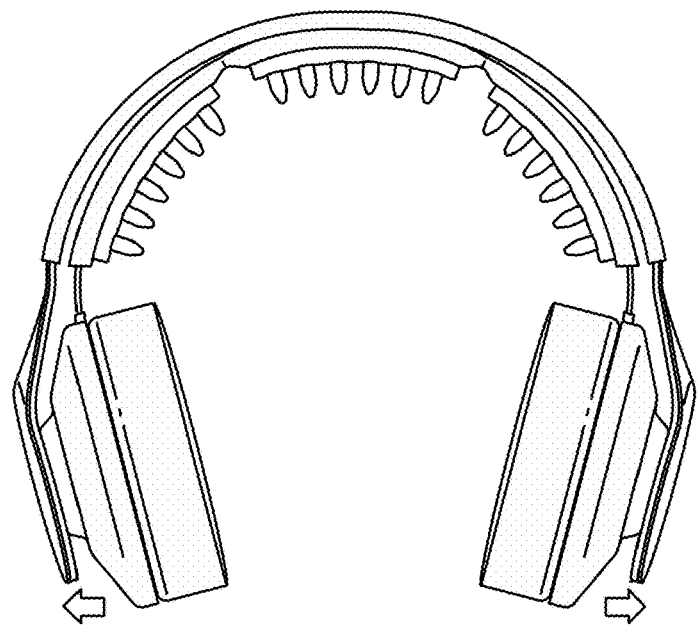
Figure 2D:
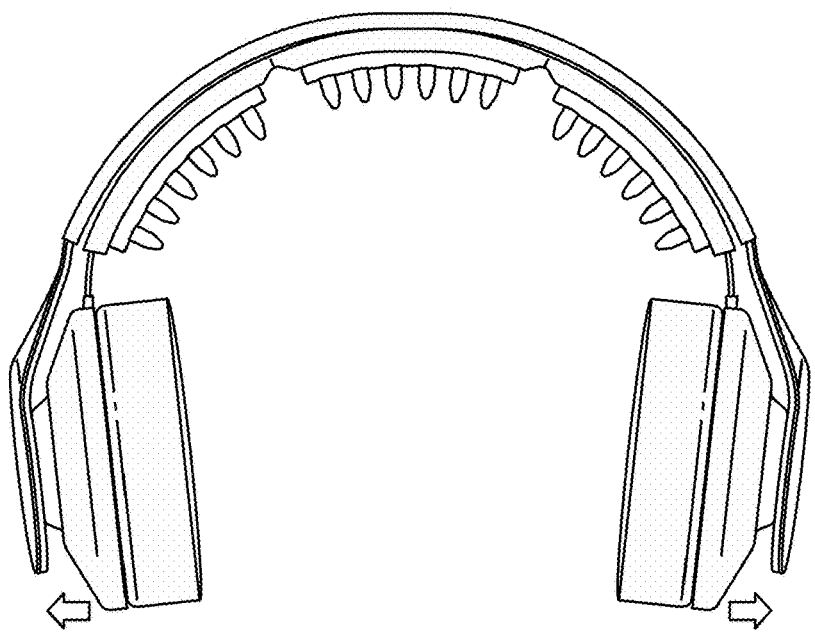

The following description of preferred embodiments of the invention is not intended to limit the invention to these preferred embodiments, but rather to enable any person skilled in the art to make and use this invention.

1. System

An embodiment of a system 100 for stimulating a user and operable at a head region of the user includes: a set of pads 110a configured at opposing head regions of the user during use of the system; a band 120a having a first end coupled to a first pad of the set of pads and a second end coupled to a second pad of the set of pads; a bridge 130a coupled the band and to an electrode 140a during use of the system; and a set of links 150a associated with the set of pads 110a, each of the set of links coupled at a first region to an interior portion of its corresponding pad, and coupled at a second region to the bridge, having an elastic modulus above a threshold modulus such that in a first operation mode, lateral displacement of the set of pads 110 produces lateral displacement of the electrode away from the head region of the user, and in a second operation mode, release of the set of pads orients protrusions of the electrode approximately normal to the head region of the user.

In one embodiment, as shown in FIG. 1, the system 100 can comprise: a set of ear pad modules 110 configured to provide a pair of anchoring points at contralateral head regions of the user; a band 120 having a first end coupled to a first ear pad module of the set of ear pad modules 110 and a second end coupled to a second ear pad module of the set of ear pad modules 110; a bridge 130 coupled to an inferior midregion of the band 120 and configured to house a set of electrodes 140 for providing electrical stimulation to the user; a set of structural links providing paths for transmitting electrical current to the set of electrodes, the set of structural links 150 coupled to interior portions of the set of ear pad modules and having an elastic modulus above a threshold modulus such that 1) in a first operation mode, lateral displacement of the set of ear pad modules 110 by the user produces lateral displacement of the set of electrodes 140 away from the head region of the user, and 2) in a second operation mode, release of the set of ear pad modules 110 by the user orients protrusions of the set of electrodes 140 approximately normal to the head region of the user.

The system 100 functions to allow a user to properly position one or more electrode units at the head of the user, wherein the electrode units include one or more flexible protrusions configured for delivery of electrical stimulation to the user. Additionally or alternatively, the system 100 can function to facilitate sensing (e.g., biometric sensing) of signals from a user in cooperation with, or in the absence of, stimulation. The system 100 can additionally or alternatively incorporate or cooperate with one or more of: transducers (e.g., optical sensors, optical emitters, ultrasonic transducers, etc.), additional sensors (e.g., temperature sensors, activity detecting sensors, sensors associated with position, velocity, or acceleration detection, biometric sensors, etc.) for sensing signals from the user, additional sensors (e.g., temperature sensors, barometric pressure sensors, light sensors, microphones, etc.) for sensing signals from the environment of the user, and any other suitable module.

In one embodiment, the system 100 thus prevents or delays deflection or bending of individual electrode protrusions into an orientation approximately tangential to the scalp of the user (e.g., during initial placement of the system 100 at the body of the user), and facilitates maintenance of a protrusion orientation during approach to the head that is more perpendicular to the scalp of the user. As such, the system 100 can control the orientation(s) at which deflectable electrode elements of the system approach the head of the user, thereby preventing early dragging of deflectable electrode elements over the hair of the user in an undesired manner during placement of the system 100 at the head of the user. Additionally or alternatively, the system 100 can provide enhanced comfort during placement of the system 100 at the head of the user, and/or provide proper positioning of elements of the system 100 at the head of the user.

In alternative embodiments, the system 100 can prevent or delay deflection/bending of individual electrode protrusions into an orientation approximately tangential to any other convex surface of a body (e.g., an anatomical region of a human or other animal), for instance, during initial placement of the system 100 at the convex surface. Furthermore, the system 100 can facilitate maintenance of a protrusion orientation during approach to the convex surface of the body that is more perpendicular to the convex surface. In such other embodiments, the system 100 can be applied to, stimulate, or otherwise sense signals from one or more of: a limb region (e.g., arm region, leg region) of the user, a gluteal region of a user, a pelvic region of a user, a torso region of a user (e.g., an abdominal region of a user, a breast region of a user), a neck region of a user, another head region of a user, or any other suitable body region of a user.

As such, the system 100 can control the orientation(s) at which deflectable electrode elements of the system approach the convex surface of the body, thereby preventing early dragging of deflectable electrode elements over the hair or other aspects of the surface in an undesired manner during placement of the system 100 at the convex surface. Additionally or alternatively, the system 100 can provide enhanced comfort during system placement, and/or provide proper positioning of elements of the system 100.

The system 100 can thus facilitate maintenance of an electrode configuration that provides desired impedance characteristics and/or a desired type of contact at the user-electrode interface during placement and/or during use of the system 100. The system can further include features configured to provide a high level of comfort in terms of wearability, as the user wears the system 100 during a period of stimulation treatment. Preferably, the system 100 is configured to interface with and position electrode units at the head of the user, such as the embodiments, variations, and examples of electrode systems described in U.S. application Ser. No. 14/878,647 entitled "Electrode System for Electrical Stimulation" and filed on 8 Oct. 2015 and/or electrode systems described in U.S. application Ser. No. 14/470,683 entitled "Electrode System for Electrical Stimulation" and filed on 27 Aug. 2014, and/or electrode systems described in U.S. application Ser. No. 29/553,732 entitled "Biointerface Electrode" and filed on 4 Feb. 2016, which are each herein incorporated in its entirety by this reference; however, the system 100 can alternatively be configured to interface with and/or position any other suitable type of electrode or functional unit at the head of the user.

The system 100 is preferably configured to be worn by a user who is away from a research or clinical setting, such that the user can wear the system 100 while he or she is in a natural setting (e.g., at home, at a gym, outdoors, etc.). The system 100 can additionally or alternatively be configured to be operated by a user who is in a research setting, a clinical setting, or any other suitable setting. Furthermore, while some embodiments of the system are configured to be worn at the head of the user, alternative embodiments of the system 100 can be configured to be worn or coupled to any other suitable body region of the user, as described above.

In some embodiments, the system 100 can implement and/or facilitate implementation of one or more embodiments, variations, or examples of the method(s) described in U.S. application Ser. No. 14/470,747 entitled "Method and System for Providing Electrical Stimulation to a User" and filed on 27 Aug. 2014 and/or U.S. application Ser. No. 15/059,095 entitled "Method and System for Providing Electrical Stimulation to a User" and filed on 2 Mar. 2016, which are each incorporated in its entirety by this reference.

As such, in embodiments and variations, the system 100 and/or method(s) can be configured for application of one or more of: transcranial electrical stimulation (TES) in the form of transcranial direct current stimulation (tDCS), transcranial alternating current stimulation (tACS), transcranial magnetic stimulation (TMS), transcranial random noise stimulation (tRNS, e.g., band-limited random noise stimulation), transcranial variable frequency stimulation (tVFS), band-limited stimulation transformed to increase RMS power while minimizing transients and clipping, and any other suitable form of TES. Furthermore, in any of the above examples and variations, the system 100 and/or method can be configured to for delivery of stimulation as anodal stimulation and/or cathodal stimulation. In other examples, the electrical stimulation can additionally or alternatively comprise any other form of electrical stimulation (e.g., electrical muscle stimulation, etc.) configured to stimulate any other suitable region of the user's body, with any suitable penetration depth, and/or any suitable tissue structure (e.g., neural, musculoskeletal).

In some variations, robust connection with the user provided by the elements (e.g., mechanical aspects) of the system 100 additionally or alternatively apply to transmission of non-electrical modes of stimulation according to other suitable methods. As such, the system 100 and/or method(s) can additionally or alternatively be configured to transmit non-electrical modes of stimulation (e.g., ultrasound stimulation, optical stimulation) by using any appropriate transducer or set of transducers in place of or in addition to electrode contacts. For instance, one variation of the system 100 can be used to provide ultrasound transducing elements at a desired body region of the user, as facilitated by an array of protrusions configured to displace obstacles to ultrasound stimulation at the body region of the user. In this variation, ultrasound transducing elements can be configured at any suitable position along a length of a protrusion and/or at a distal end of a protrusion. Other variations can, however, be configured to incorporate any other element(s) for stimulating the user.

However, the system 100 can implement or facilitate implementation of any other suitable method(s).

1.1 System—Anchoring Position Elements

The set of pads 110a/ear pad modules 110 functions to provide a pair of anchoring points at contralateral head regions (or other opposing body regions) of the user. The set of pads 110a/ear pad modules 110 can also function to enhance comfort of the system 100 as the system 100 is being worn by the user. Additionally or alternatively, the set of pads 110a/ear pad modules 110 can be configured to provide desired audio output functions (e.g., in terms of sound quality, in terms of noise cancelling, etc.) in variations of the system 100 configured with one or more speaker elements.

As such, in variations where the pads comprise ear pad modules 110, each of the set of ear pad modules preferably comprises a region of compliant material configured to interface with the head of the user, in proximity to an ear of the user in order to provide comfort, and a rigid portion configured to facilitate maintenance of contact between the user and the system during use. The compliant/padded portions of the ear pad modules can be circumaural, or can alternatively be supra-aural. In one variation, the set of ear pad modules can produce a headphone-type form factor; however, the set of ear pad modules can alternatively contribute to any other suitable form factor for the system 100. In one such alternative variation, the set of ear pad modules can provide an earphone-type form factor. Still alternatively, the set of ear pad modules can be substituted with or supplemented with any suitable element(s) that provide(s) anchoring points at the head of the user, and may not provide anchoring points at contralateral head regions of the user (e.g., the system can be asymmetric in form factor, or may provide anchoring points at other anatomically-opposing locations, such as inion and frontal pole of the head). In one such set of alternative examples, the set of ear pad modules can be substituted with pads/housing configured to produce anchoring points at the body of the user by one or more of: friction, adhesives (e.g., mild adhesives), biasing forces, hair grabbers (e.g., hair clips, hair ties, etc.), and any other suitable mechanism.

The pads/ear pad modules can be modular and include portions configured to provide structure/protection, and portions configured for user comfort. For instance, some variations of the pads/ear pad modules can comprise pad modules including an outer housing 112 (i.e., lateral portion) that provides structural support for coupling to other elements of the system 100 and/or supports a medial compliant portion 113 that interfaces with the body of the user. In variations, the outer housing 112 can be composed of a rigid material (e.g., plastic, metal, wood, ceramic, glass, etc.), while the medial portion 113 can be composed of a compliant material (e.g., foam, sponge, fabric, air/fluid/hydrogel/gel filled sac, etc.). However, variations of the system 100 can additionally or alternatively omit outer housings 112 and/or medial compliant portions 113 for the pad modules. Furthermore, the pads/ear pad module can additionally or alternatively be configured in any other suitable manner.

In one specific example, as shown in FIGS. 2A-2D, each of the set of ear pad modules 100 preferably comprises a padded medial portion configured to interface with the head of the user, and a rigid lateral portion, coupled to (e.g., partially housing) the padded medial portion and configured to interface with the band 120 of the system 100, as described in more detail below. In the specific example, the padded medial portion is configured to be filled with a compliant material and circumaural, such that the set of ear pad modules 110 substantially surround the ears of the user and provide comfortable anchoring points approximately centered at the ear regions of the user.

In this example, each of the set of ear pad modules can be configured to be acoustically transparent, or to have a high degree of acoustic transparency, such that the user can still hear sounds from the environment of the user, while using the system (e.g., in an application wherein the user is an athlete and needs to hear instructions from a coaching entity). As such, this specific example can be applied to situations where the user is undergoing a session of electrical stimulation (e.g., transcranial stimulation) while receiving instruction and/or performing tasks in coordination with receiving instruction from an entity (e.g., coaching entity, electronic device providing instructions, etc.) in proximity, in the environment of the user. As such, this specific example of the system 100 can comprise pads (e.g., at a medially-oriented compliant portion of an ear pad module) that are not configured for sound isolation, noise cancelling, or noise reduction during operation of the system 100.

In a variation of this example, each of the set of ear pad modules can be configured to have a low degree of acoustic transparency, or to cooperate with other electronics of the system 100 to provide sound isolation, noise reduction, or noise cancelling for the user, or to provide isolation from undesired sounds for the user while also providing desired sounds (such as music or instructions) to the user (e.g., using speakers, electronic amplification, wireless or wired transmission of audio signals, etc.). As such, this specific example can be applied to situations where the user is undergoing a session of electrical stimulation (e.g., transcranial stimulation) while receiving instruction and/or performing tasks in coordination with receiving instruction through audio output elements (e.g., speakers) integrated with the set of ear pad modules 110a or otherwise integrated with the system 100. However, variations of the specific example can alternatively be configured in any other suitable manner.

In either of these examples, the configuration of the system 100 and set of pads 110a/110 can be configured to facilitate stimulation delivery/training in the context of motor skill training including one or more of: athletic training (e.g., team sports training, individual sports training), motor skill rehabilitation training (e.g., stroke rehabilitation training, etc.), military training (e.g., army training, air force training, marine corps training, navy training, coast guard training), motor skill training (e.g., surgeon training), and/or any other suitable type of motor skill training.

As described in further detail below, the configuration of the system 100 and set of pads 110a/110 can be configured to facilitate stimulation delivery/training in any other suitable context (e.g., focus, memory, learning, etc.), depending upon the brain region(s) stimulation and/or the type(s) of stimulation applied.

1.2 System—Band

The band 120 is configured to have a first end coupled to a first pad module of the set of pad modules 110 and a second end coupled to a second pad module of the set of pad modules 110, and functions to support the set of pad modules, and facilitate biasing of the system 100 into coupling with the head of the user. The band 120 is preferably composed of a rigid material that is elastically deformable within the range of deformation needed to allow the user to wear the system, such that the user can induce a deformation of the band 120 in the process of donning the system 100, and the system 100 can elastically recover and provide a biasing force that facilitates coupling of the system 100 at the head of the user. Variations of operation modes of the system 100 in relation to coupling of the system 100 to the user are described in more detail below. However, the band 120 can alternatively be inelastically deformable in some manner to facilitate coupling of the system 100 to the user.

As such, in variations, the band 120 can be composed of a polymeric material (e.g., a plastic, etc.) and/or a metallic material that exhibit(s) properties of elastic deformation. Additionally or alternatively, the band 120 can be composed of a material that has ductile properties or brittle properties. The band 120 can comprise a single material, or can comprise a composite of different materials (e.g., with regions or layers of different materials).

Figure 3:
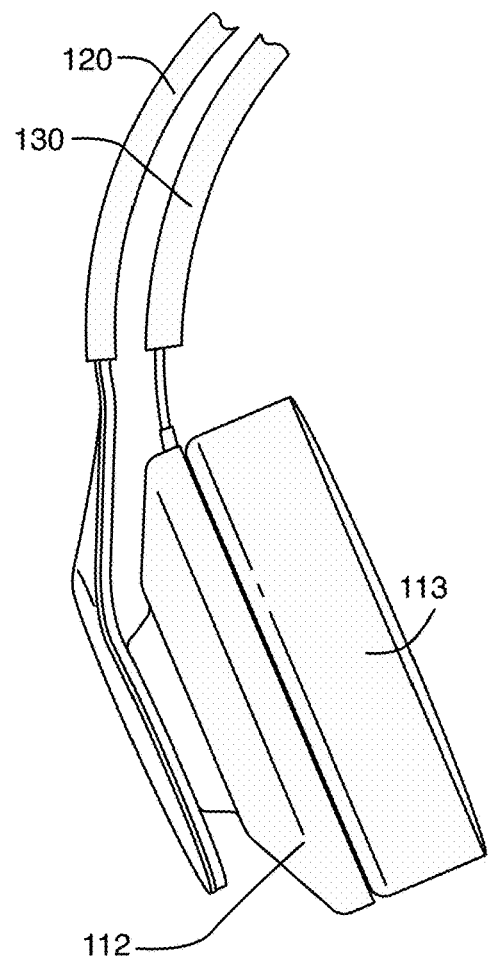
FIG. 3 depicts a portion of an embodiment of an electrode positioning system.

The band 120 is preferably of unitary construction and continuous across its length and/or its width; however, the band 120 can alternatively be modular and comprise one or more components that couple together in a physically coextensive manner (e.g., in a press fit, in a snap fit, with adhesives, with magnetic coupling, etc.) to form the band 120. Additionally or alternatively, in some variations, the band 120 can be configured to have parts that bend relative to each other (e.g., with a hinge), in order to transition the system 100 between a compact/storage mode and an in-use mode. As noted above, the band 120 preferably has a first end coupled to a first pad module of the set of pad modules 110 and a second end coupled to a second pad module of the set of pad modules 110, such that the band traverses laterally over the frontal bone and/or the parietal bone of the user's skull, and supports the pad modules 110 at the ears of the user. In one variation of this configuration, the first end of the band 120 can couple to an exterior (e.g., lateral) surface of the first ear pad module (e.g., an outer housing 112 portion of the first ear pad module), and the second end of the band 120 can couple to an exterior (e.g., lateral) surface of the second ear pad module (e.g., an outer housing 112 portion of the second ear pad module), an example of which is shown in FIG. 3 (with only one of the two ends of the band shown). In the specific example, the band 120 can comprise an interior plastic layer coupled to an exterior metal layer (e.g., steel layer), wherein bonding of the plastic layer to the metal layer provides a composite that has desired elastic deformation properties in relation to coupling of the system 100 to the user. However, variations of the specific example of the band can additionally or alternatively comprise any other suitable material(s) composition and/or be configured in any other suitable manner.

In some variations, the band 120 can include a longitudinal expansion mechanism that allows the length and/or radius of curvature of the band 120 to be adjusted to different head sizes. In variations, the longitudinal expansion mechanism can include one or more of: sleeves, extendable (e.g., stretchable) materials, linking elements (e.g., links), and any other suitable expansion element(s). In a specific example, the longitudinal expansion mechanism can comprise concentric or otherwise loosely coupled sleeves that allow lengthening of the band 120 to one or more positions (e.g., with a ratcheting mechanism, with a detent mechanism, with a locking mechanism, etc.). Furthermore, the longitudinal expansion mechanism can cooperate with lengthening functions of the set of structural links 150 described below, in order to allow lengthening of the band 120 in parallel with lengthening functions of the set of structural links 150.

1.3 System—Bridge

The bridge 130 is configured to couple to the band 120 and functions to support one or more electrodes for providing electrical stimulation to the user. As such, the bridge 130 preferably includes regions that facilitate electrical and/or mechanical coupling of one or more electrode units to the bridge 130 (e.g., at an interior surface). Preferably, the bridge 130 is configured to couple to an inferior midregion of the band in a manner that allows outward displacement of lateral end regions of the band 130 during use of the system 100; however, the bridge 130 can additionally or alternatively be configured to couple to the band 120 and/or any other element of the system 100 in any other suitable manner.

In one variation, the bridge 130 is configured to house at least one of a set of electrodes 140 for providing electrical stimulation to the user, in a configuration wherein an interior surface of the bridge 130 includes recesses corresponding to the set of electrodes 140 and electrical/mechanical coupling elements proximal to the recesses to robustly retain the electrodes 140 and provide current for electrical stimulation of the user through the electrodes 140. In this variation, the set of electrodes 140 can include a pair of contralateral electrodes (i.e., lateral electrodes) configured to be positioned proximal contralateral motor/pre-motor cortices of the user during operation of the system. Additionally or alternatively, in this variation, the set of electrodes 140 can include a middle electrode configured to be positioned midway or substantially midway between lateral electrodes and thus coupleable to a midregion of the bridge 130 (e.g., within a recess at a midregion of the inferior surface of the bridge 130).

As indicated above, the set of electrodes 140 preferably comprise embodiments, variations, and/or examples of the electrode units described in U.S. application Ser. No. 14/878,647 entitled "Electrode System for Electrical Stimulation" and filed on 8 Oct. 2015 and/or electrode systems described in U.S. application Ser. No. 14/470,683 entitled "Electrode System for Electrical Stimulation" and filed on 27 Aug. 2014, and/or electrode systems described in U.S. application Ser. No. 29/553,732 entitled "Biointerface Electrode" and filed on 4 Feb. 2016, which can be configured for transcranial electrical stimulation of a user in various modes. As such, one or more of the set of electrodes 140 can include: an array of permeable bodies configured to absorb and deliver a solution that facilitates electrical coupling between the system and a body region of the user; a housing supporting the array of permeable bodies; and a coupling subsystem comprising a first electrical coupling region in electrical communication with the array of permeable bodies at an interior portion of the housing and a second electrical coupling region, configured to couple the first electrical coupling region to the electronics subsystem of the system 100.

However, the bridge 130 (or other portion of the system 100) can additionally or alternatively be configured to support elements for any other suitable type of stimulation, therapy, or sensing for the user. The set of electrodes 140 can be configured to magnetically couple to the bridge 130 in a manner such as that described in U.S. application Ser. No. 14/878,647, where the bridge includes one or more magnets and the set of lateral electrodes include one or more incorporated ferromagnets that are complementary to the magnet of the bridge 130. However, the electrodes 140 can magnetically couple to the bridge 130 in an alternative manner, or can alternatively be configured to mechanically couple to the bridge 130 in any other suitable manner. Furthermore, the bridge 130 can be configured to interface with one or more electrode units (e.g., an electrode unit centrally located between a set of lateral electrodes) in addition to the set of lateral electrodes 140.

In more detail, in relation to a middle electrode, the system 100 can be configured to ensure that laterally positioned electrodes 140 maintain proper contact with their corresponding head regions of the user (e.g., the scalp of the user), while ensuring that middle electrode also maintains good contact with its corresponding head region of the user. Thus, ensuring proper contact between all electrodes of the system 100 and their corresponding head regions of the user further constrains design of the system 100.

Preferably, the set of electrodes 140 includes electrode units that are configured to be positioned at contralateral head regions of the user, and in a specific example, the bridge 130 can be configured to position the set of lateral electrodes for stimulation of contralateral motor cortex regions of the user's brain. The bridge 130 can, however, be configured to support and facilitate positioning of the electrode unit(s) for stimulation of any other suitable brain regions of the user. As described in U.S. application Ser. No. 14/878,647, the electrode units can have one or more protrusions supporting permeable bodies or otherwise deflectable elements that facilitate delivery of electrical stimulation to the user, and mechanical interactions between the bridge 130 and other elements of the system 100 (e.g., the band 120, the set of structural links 150, etc.) can prevent deflection or bending of individual protrusions into an orientation approximately tangential to the scalp of the user. Thus, the bridge 130 can, along with other portions of the system 100, facilitate maintenance of an electrode protrusion orientation that is more perpendicular to the scalp of the user in producing desired impedance characteristics and/or a desired type of contact at the user-electrode interface.

Furthermore, in relation to the set of electrodes 140, one or more portions of the system 100 (e.g., the bridge 130, the band 120, etc.) can additionally or alternatively be configured to couple to an electrode unit 145 (e.g., electrode pad, electrode sponge, electrode with protrusions, etc.) that interfaces with a frontal or prefrontal cortex region of the user during operation of the system 100. For instance, the electrode unit can include a cable providing a mechanical/electrical pathway that couples the electrode-user interface (e.g., electrode pad, electrode sponge, electrode with protrusions, etc.) to electronics of the system 100. In specific examples, a first end of the cable can plug into the bridge 130 or the band 120 to access the current source of an electronics system, and a second end of the cable can connect to the electrode portion that interfaces with the user. However, the set of electrodes 140 can additionally or alternatively include any other suitable electrodes.

Similar to the band 120, the bridge 130 is preferably composed of a rigid material that is elastically deformable within the range of deformation needed to allow the user to wear the system 100, such that the user can induce a deformation (e.g., outward deflection) of the bridge 130 in the process of donning the system 100, and the system 100 can elastically recover and provide a biasing force that facilitates coupling of the set of lateral electrodes 140 at the head of the user.

Preferably, the bridge 130 is indirectly coupled to the band 120 through one or more other elements of the system (e.g., the set of links 150, the set of pad modules 110, etc.), in order to allow lateral displacement of the end regions of the band 120 to affect lateral displacement of regions of the bridge 130 associated with the set of electrodes 140; however, the bridge 130 and the band 120 can additionally or alternatively be directly coupled to each other in order to have coupled deformation behavior across the band 120 and the bridge 130. In relation to deformation of the bridge 130, the bridge 130 can thus be indirectly induced to deform due to coupling between the bridge 130 and the set of ear pads 110 (by way of the set of structural links 150 described in more detail below), and coupling between the set of ear pads 110 and the band 120; however, the bridge 130 can alternatively be induced to deform during electrode positioning at the body region of the user in any other suitable manner, variations and examples of which are described below. Furthermore, variations of operation modes of the system 100 in relation to coupling of the system 100 to the user are described in more detail below.

Similar to the band 120, the bridge 130 can be composed of a polymeric material (e.g., a plastic, etc.) and/or a metallic material that exhibit(s) properties of elastic deformation. Additionally or alternatively, the bridge 130 can be composed of a material that has ductile properties or brittle properties with joints or hinged regions to allow the bridge 130 to outwardly deflect, as described in more detail below, or the bridge 130 can be composed of a material that exhibits properties at least partially of plastic deformation, so that the bridge can be deformed to conform with the head of a user. The bridge 130 can comprise a single material, or can comprise a composite of different materials (e.g., with regions or layers of different materials).

Figure 4:
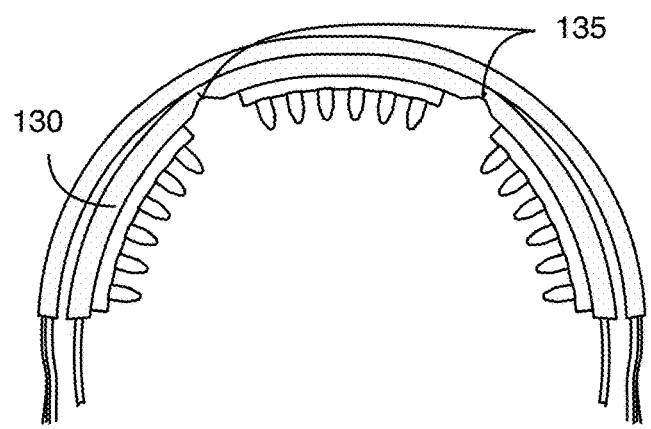
FIG. 4 depicts a portion of an embodiment of an electrode positioning system.

As noted above, the bridge 130 can comprise a set of joints 135 that allow portions of the bridge to bend at defined positions (e.g., as hinges), an example of which are shown in FIG. 4. In one variation, the set of joints 135 can be positioned between adjacent electrode positions (e.g., two adjacent electrode positions) defined by the bridge 130, such that the bridge is configured to flex at inter-electrode positions (e.g., in variations in which substrate portions of the electrodes 140 are substantially rigid). However, in variations wherein substrate or other portions of the electrodes 140 exhibit low rigidity, the set of joints 135 can comprise joints configured at intra-electrode positions of the bridge 130. The set of joints 135 are preferably evenly spaced, but can alternatively comprise non-evenly spaced joints. In one variation, the set of joints 135 can comprise regions thinner than a characteristic thickness of the bulk of the bridge 130. In another variation, the set of joints 135 can comprise regions of material having lower stiffness than that of non-joint regions of the bridge 130. In still another variation, the set of joints 135 can comprise physical hinge elements coupling adjacent pieces of the bridge 130, such that the hinges allow bending between portions of the bridge 130 at the hinges. However, the set of joints 135 can alternatively be defined in any other suitable manner. Furthermore, in some variations, the bridge 130 may alternatively omit a set of joints, such that the bridge 130 can deform continuously across the span of the bridge 130.

As noted above, the bridge 130 preferably couples to the band 120 at an inferior surface of the band 120, in order to provide a fixed region relative to which opposing ends of the bridge 130 can deflect. However, variations of the bridge 130 can alternatively have 110 direct coupling to the band 120, and instead rely upon other elements of the system 100 (e.g., structural links, pad modules, etc.) for deflection of the bridge 130 in response to outward displacement of end regions of the band 120 and/or pad modules 110.

In variations with direct coupling between the bridge 130 and the band 120, the bridge 130 can couple to the band 120 at a midregion of the inferior surface of the band 120; however, the bridge 130 can additionally or alternatively couple to any other suitable portion of the band 120 that provides desired relative bending behavior between the bridge 130 and the band 120, or provides a desired spatial relationship between the band 120 and bridge 130 in order to bring electrodes 140 into proximity with a desired anatomical target. In variations, the bridge 130 can couple to the band 120 using any one or more of: mechanical fasteners (e.g., screws, bolts), adhesives, thermal bonding, magnetic coupling, and any other suitable manner. In a specific example, the bridge 130 can couple to the band 120 by way of a set of fasteners (e.g., screws, bolts, etc.) that substantially lock the position of the bridge 130 in place relative to the band 120 at the fixed region. In the specific example, the footprint of the bridge 130 is also contained within the footprint of the band 120; however, variations of the example of coupling between the bridge 130 and the band 120 can be configured in any other suitable manner.

In relation to the band 120, the bridge 130 preferably has a characteristic radius of curvature that is smaller than the radius of curvature of the band 120, wherein the radius of curvature of the bridge 130, while the system 100 is worn by the user, is complementary to the radius of curvature of the user's head. As such, morphology of the bridge 130 provides a substantially continuous and robust interface between surfaces of the set of electrodes 140 and the head region(s)

of the user involved in the stimulation therapy process. However, as indicated above and below, the bridge 130 and the band 120 can alternatively have any other suitable morphology and/or be configured relative to each other in any other suitable manner that allows a proper electrode-user interface (e.g., in terms of impedance) to be provided by the system 100.

1.4 System—Links

Each of the set of links 150 is preferably coupled to the bridge 130 and to a corresponding ear pad module of the set of ear pad modules, and collectively can function to perform one or more of the following: 1) indirectly facilitate lengthening of the band 120 with the longitudinal expansion mechanism described above (by allowing other portions of the system 100 to extend); 2) provide electrical paths for transmitting electrical current to the set of lateral electrodes coupled to the bridge 130 or from one ear pad module to a second ear pad module (by electrically conductive elements coupled to or otherwise integrate with the links); and 3) provide desired mechanical behavior that prevents undesired deformation of portions of the set of electrode units 140 as the user dons the system 100. Furthermore, the set of links 150 can cooperate with other elements of the system 100 to provide a partial coupling mechanism that allows outward deflection of the set of ear pad modules 110 to induce some outward deflection of the set of electrodes 140 (i.e., lateral electrodes), by way of the bridge 130. In more detail, the partial coupling mechanism can allow the bridge 130 and coupled electrodes 140 to independently conform to the shape of the head of the user without being fully constrained by the band 120 (or other elements of the system 100. One or more of these functions can, however, be enabled using variations of elements of the system 100 described above, additional variations of elements of the system 100 described in Section 1.5 below, and/or any other suitable additional element(s).

The set of links 150 is preferably coupled to interior portions (e.g., medial portions of the outer housing 112) of the set of pad modules 110 and preferably, each of the set of structural links 150 has a characteristic stiffness (in terms of elastic modulus) above a threshold modulus such that 1) in a first operation mode, lateral displacement of the set of pad modules 110 by the user produces displacement of the set of electrodes 140 away from the head region of the user in a direction approximately normal to the surface of the head region, and 2) in a second operation mode, release of the set of pad modules 110 by the user brings protrusions (i.e., permeable bodies, protrusions supporting the permeable bodies) of the set of electrodes 140 into contact with the head region of the user along a path approximately normal to the surface of the head region of the user. In more detail, transitioning between the first operation mode and the second operation mode is associated with donning of the system 100 by the user, such that lateral electrodes coupled to the bridge 130 are properly positioned at the head of the user with minimal-to-no-bending of flexible protrusions of the electrodes into undesired configurations (e.g., flattened or tangential configurations).

Preferably, as described briefly above, each of the set of links 150 has a first region coupled to a corresponding pad module of the set of pad modules 110 (e.g., at an outer housing 112), and a second region coupled to a corresponding lateral portion of the bridge 130 (e.g., an end region of the bridge 130), such that outward deflection of arms of the band 120 produces outward deflection of the bridge 130 (due to indirect coupling between the band 120 and the bridge 130, by way of the set of pad modules 110). However, either or both the band 120 and the bridge 130 can be coupled to the set of ear pad modules 110 at any other suitable region(s), and/or in any other suitable manner. Furthermore, in some variations, the bridge 130 can be directly coupled to the band 120 in order to couple their applied force-induced deflection responses together, with or without coupling of the bridge 130 to the set of ear pad modules 110 by the set of structural links 150, one specific example of which is described in Section 1.5 below.

As noted above, each of the set of links 150 is substantially stiff (e.g., in terms of elastic modulus), such that forces that produce outward displacement of the set of ear pad modules 110 from each other, and that correspondingly produce bending moments at along each of the set of structural links 150 (e.g., at junctions between the set of pad modules 110 and the set of links 150 and at junctions between the set of structural links 150 and the bridge 130) result in a low level of deflection (e.g., bending without buckling) along the length of a respective structural link (i.e., relative to endpoints of the structural link). As such, during use, when the user provides an outward biasing force by pulling the set of ear pads 110 apart, lateral portions of the bridge 130 are able to deflect outward away from the head of the user in parallel with outward deflection of lateral portions of the band 120. As a result, lateral electrodes housed within the bridge 130 are displaced away from the scalp of the user, such that the donning of the system 100 cannot induce shear within each protrusion of the set of lateral electrodes 140 that would otherwise bend flexible protrusions into undesired orientations (e.g., orientations that prevent the protrusions from penetrating hair of the user).

In variations, the set of links 150 are composed of materials that can elastically deform within the range of deformation induced during normal use of the system 100; however, the set of structural links 150 can additionally or alternatively include regions or materials that have inelastic deformation or brittle properties within the range of deformation induced during normal use of the system 100. In some variations, the set of links 150 can comprise one or more of a metallic material (e.g., steel, nitinol, etc.) and a polymeric material; however, in alternative variations, the set of structural links 150 can be composed of any other suitable material. Additionally or alternatively, the set of links 150 can comprise cables, such as flexible printed circuit material or one or more individual electrical conductors substantially surrounded by an insulating material (e.g., sheath) such as overmolded thermoplastic resin or silicone rubber. As such, the set of links 150 can have structural properties and facilitate electrical coupling between different portions of the system 100.

As indicated above, the set of links 150 can facilitate lengthening of portions of the system 100 related to proper sizing of the system 100 relative to heads of different users. As such, the set of links 150 is preferably able to facilitate lengthening of the band 120 according to variations of the longitudinal expansion mechanism described above. In one such variation, each of the set of structural links 150 has an adjustable exposed length between the bridge 130 and an ear pad module, wherein extra lengths of the set of links 150 are contained within, but able to be extracted from, one or more of the bridge 130 and the set of pad modules 110. Thus, during operation, relative displacement between the set of ear pad modules and the band modulates an exposed length of each of the set of structural links. As such, in a specific example, unexposed lengths of a link of the set of links 150 can be contained within, at, or otherwise proximal to an exterior housing 112 of a pad module, or contained within, at, or otherwise proximal to an end region of the bridge 130.

In an alternative variation, each of the set of links 150 can be configured to elastically extend (e.g., as in a spring or elastomer with an appropriate spring constant) along a longitudinal axis, while still preventing undesired amounts of non-axial deflection or buckling in response to outward displacement of the set of ear pad modules 110. However, the set of links 150 can facilitate lengthening of the band 120 in any other suitable manner.

Furthermore, in variations of the system 100 where the band 120 is non-extendable, or in variations of the system 100 where partial coupling between the bridge 130 and the band 120 is provided by a set of links 150 that connect to a non-extendable region of the band 120, the set of links 150 may or may not be involved in aspects of the system 100 related to size-adjustability for different users.

As indicated above, the set of links 150 can also function to provide electrical paths for transmission of current to electrodes coupled to the bridge, wherein the electrical paths have endpoints at 1) electronics involved in generation of the desired type of stimulation and/or electrode detection and 2) regions of coupling to the set of electrodes at the bridge 130. As such, the set of structural links 150 can enable stimulation of the user through the set of electrodes 140, and/or detection of electrodes coupled to the bridge 130, variations and examples of which are described in U.S. application Ser. No. 14/878,647 entitled "Electrode System for Electrical Stimulation" and filed on 8 Oct. 2015 and/or electrode systems described in U.S. application Ser. No. 14/470,683 entitled "Electrode System for Electrical Stimulation" and filed on 27 Aug. 2014, and/or electrode systems described in U.S. application Ser. No. 29/553,732 entitled "Biointerface Electrode" and filed on 4 Feb. 2016. In more detail, electrical paths from the electronics system, through the set of links, and to interfaces between the bridge 130 and the set of electrodes 140 can allow for proper application of desired stimulation waveform patterns to the user.

Additionally or alternatively, in variations, the set of links 150 can function to provide electrical paths for transmission of energy and/or signals from one ear pad module of the set of ear pad modules 110 to another ear pad module, for example, to carry current from a battery to a control circuit, or to carry an audio signal from an audio input to a speaker. Alternative variations of the set of structural links 150 may, however, not provide electrical paths between electronics of the system 100 and the set of electrodes coupled to the bridge 130.

In a first specific example, as shown in FIGS. 2A-2D, each of the set of links comprises a cable that has a first region coupled to a medial portion of an exterior plastic housing 112 of a corresponding ear pad module, and couples, at a second region to a lateral arm of the bridge 130 (e.g., at an end region of the bridge 130. In the specific example, each cable is characterized by a stiffness value that prevents undesired amounts of non-axial deflection or buckling in response to outward displacement of the set of ear pad modules 110. Furthermore, each of the set of links 150 is involved in lengthening of the band, such that the length of a cable between an ear pad module and the bridge 130 can be adjusted according to the size of the user's head. In the specific example, each of the set of links 150 further provides an electrical path to at least one electrode coupled to the bridge 130.

Figure 5A:
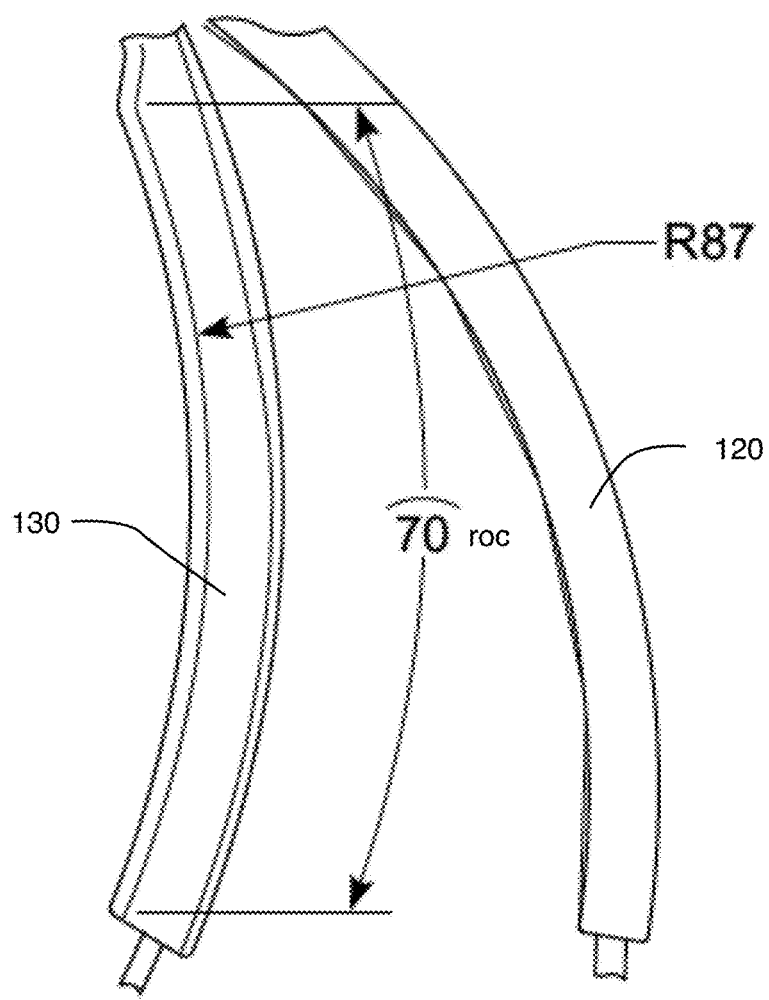
FIGS. 5A-5H depict features of a specific example of an electrode positioning system.
Figure 5B:
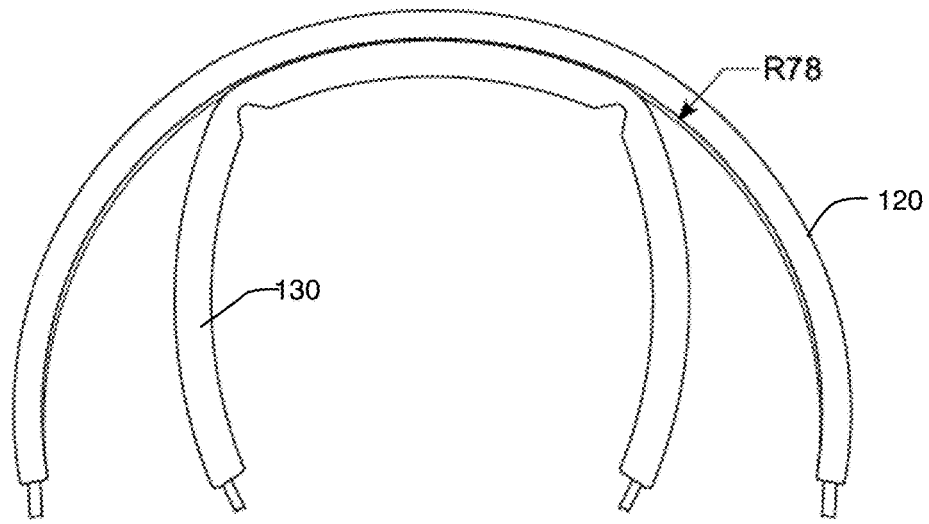
Figure 5C:
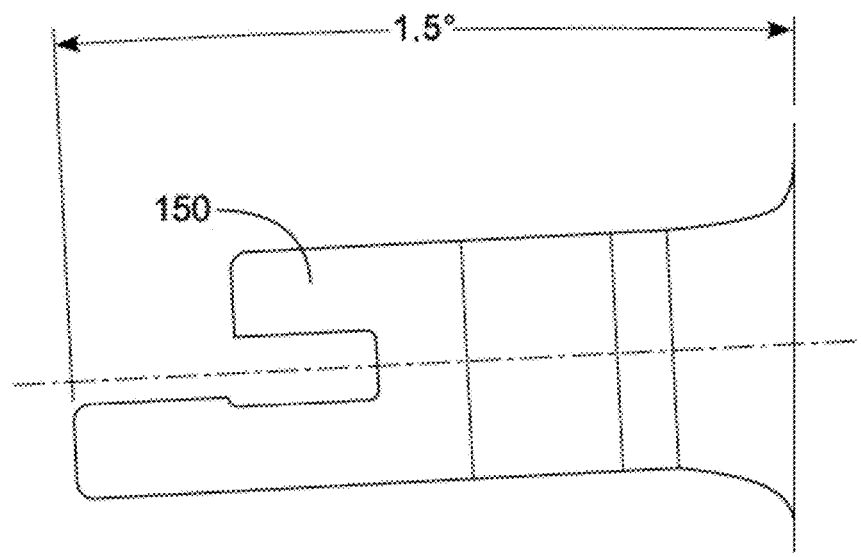
Figure 5D:
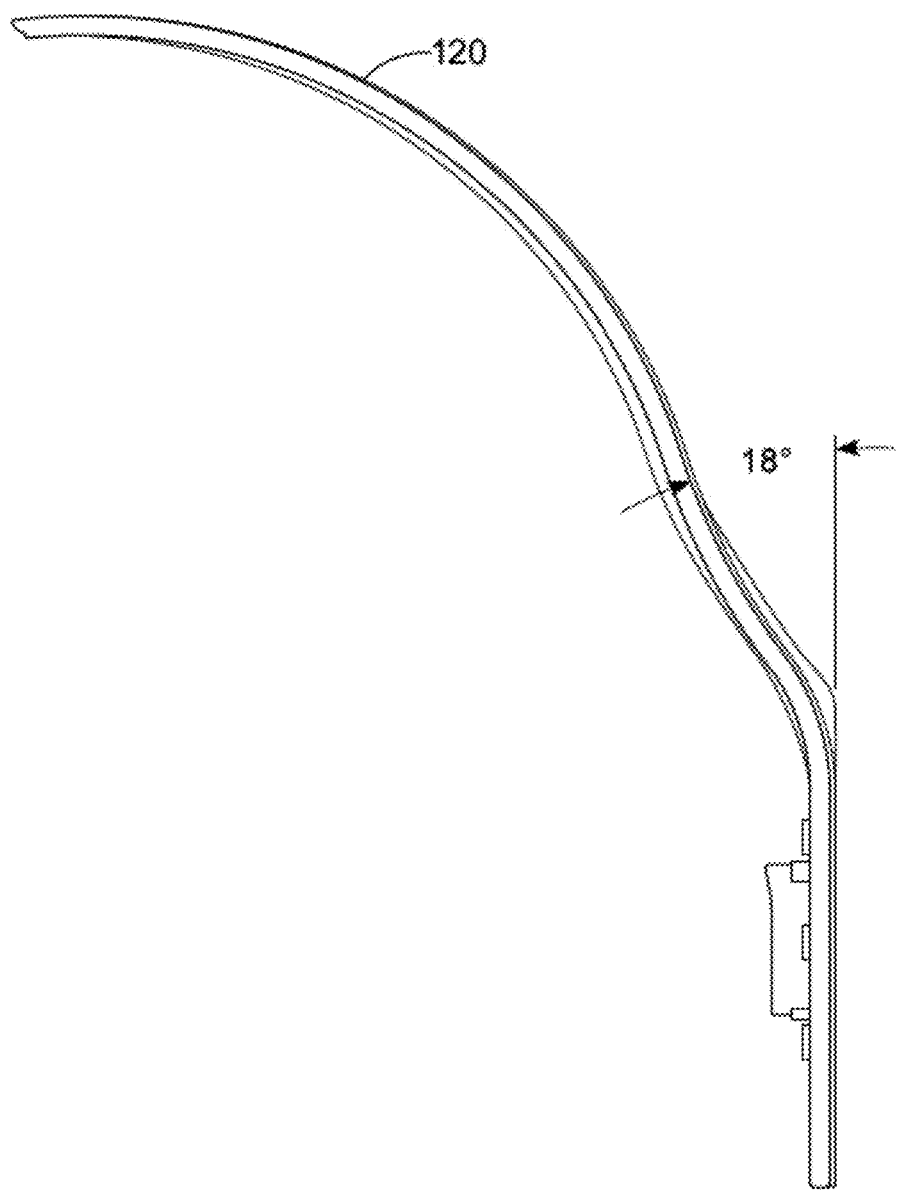
Figure 5E:
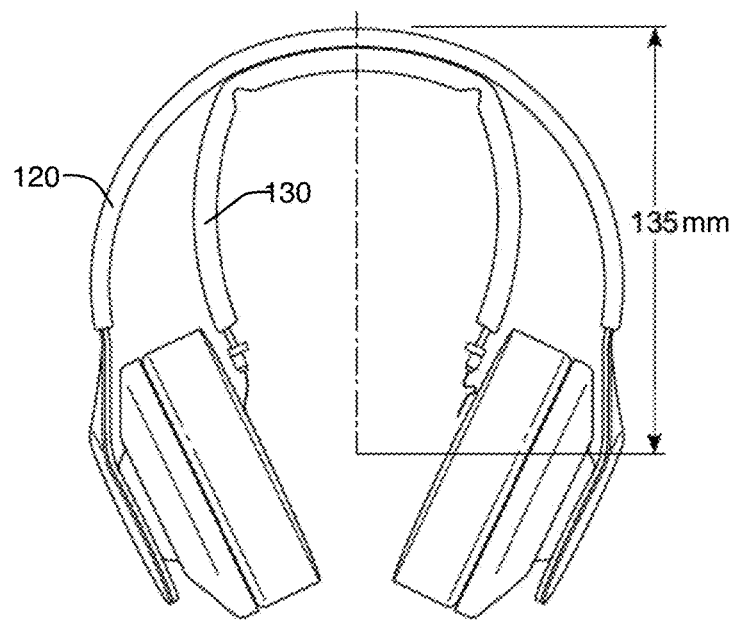
Figure 5F:
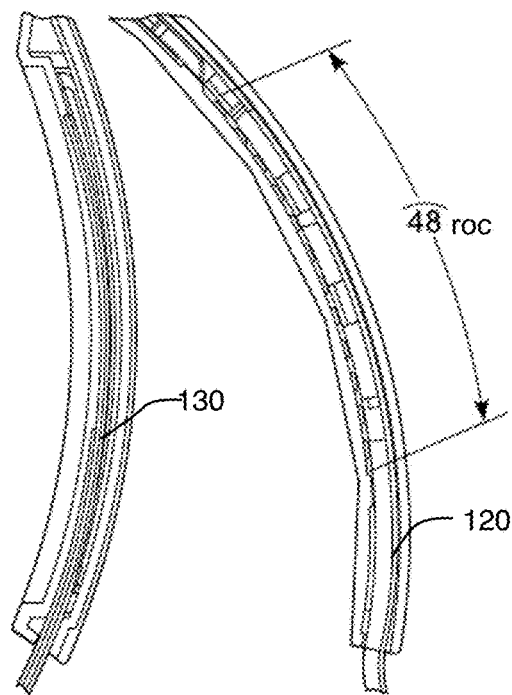
Figure 5G:
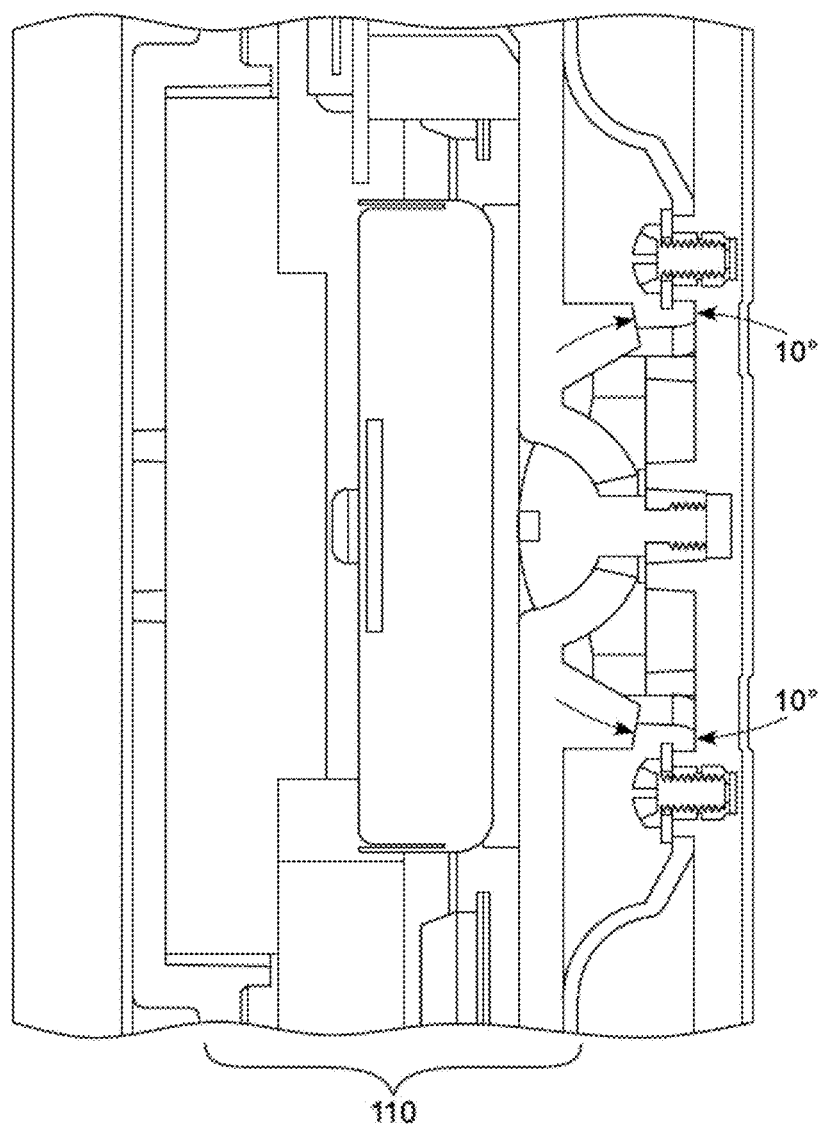
Figure 5H:
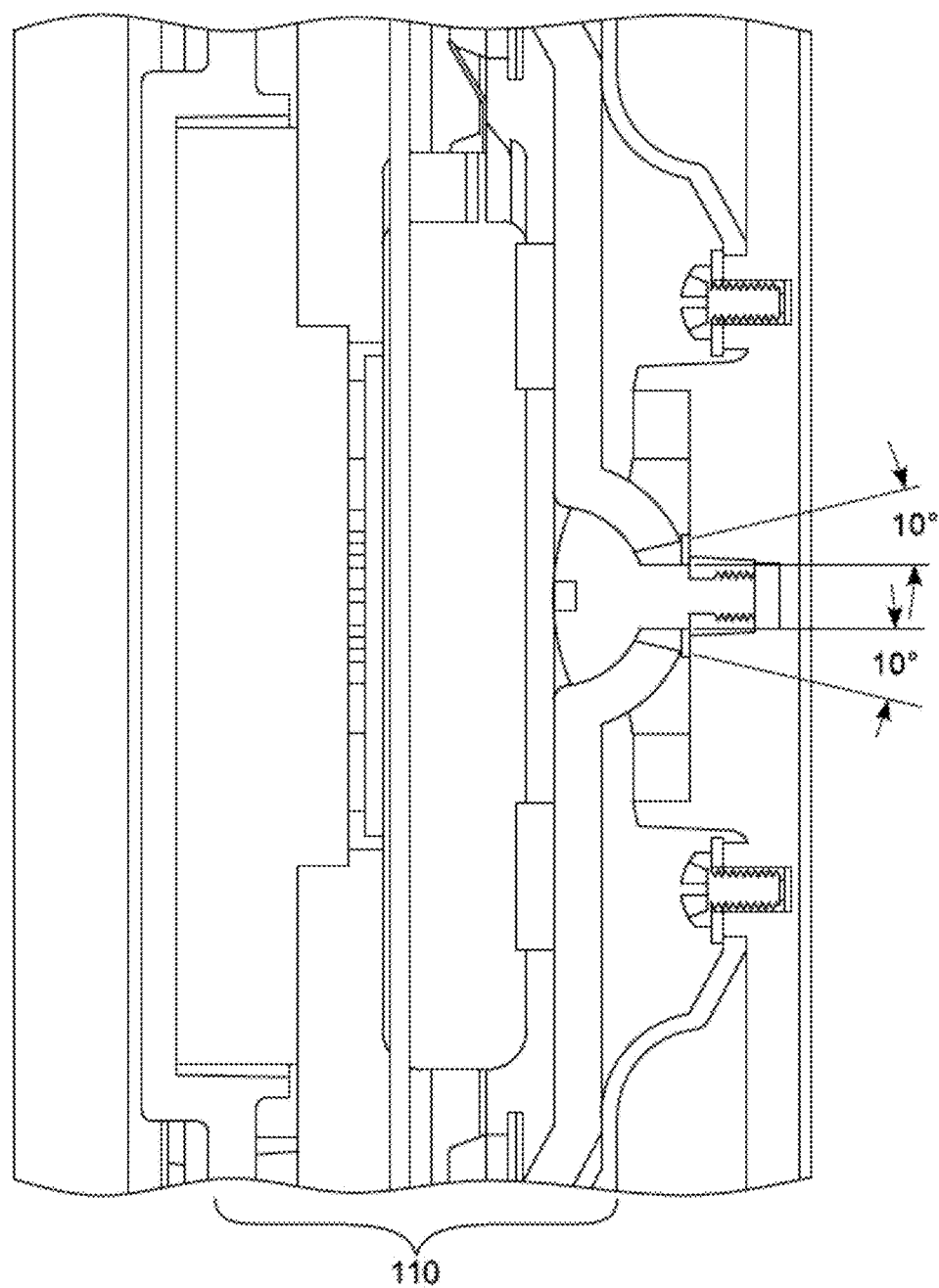
Figure 6A:
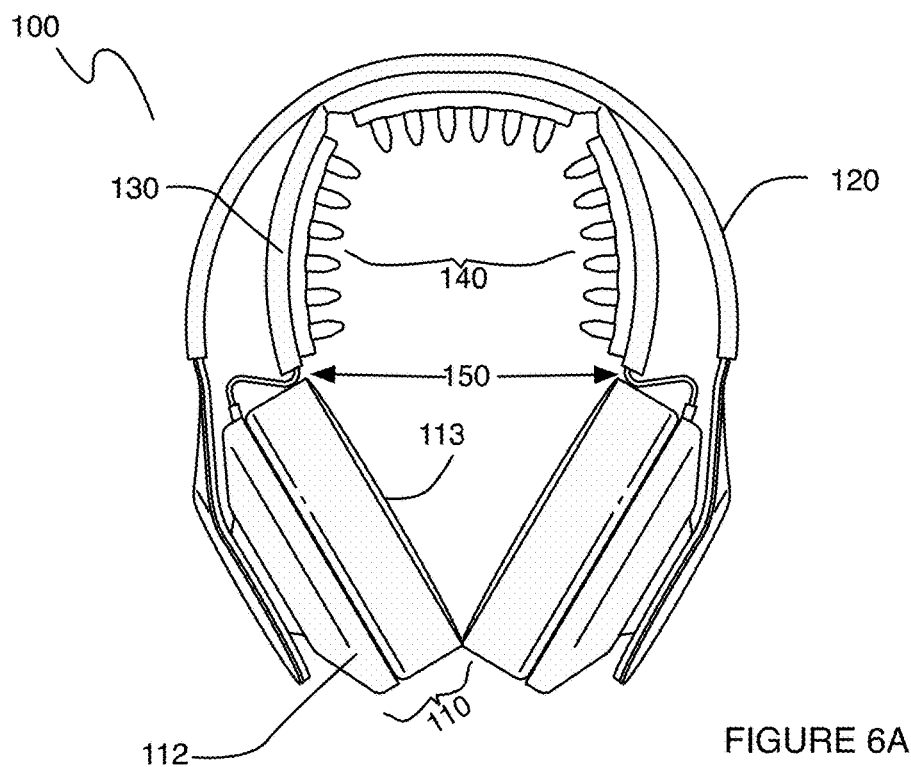
FIGS. 6A-6D depict a second specific example of an embodiment of an electrode positioning system.
Figure 6B:
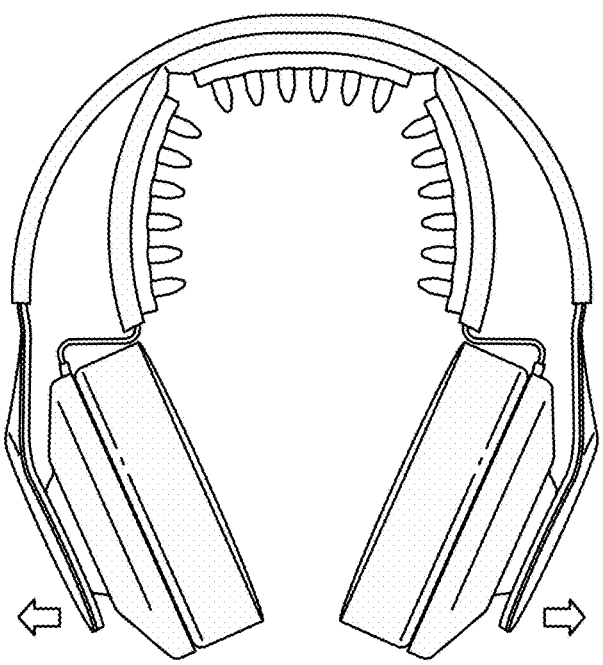
Figure 6C:
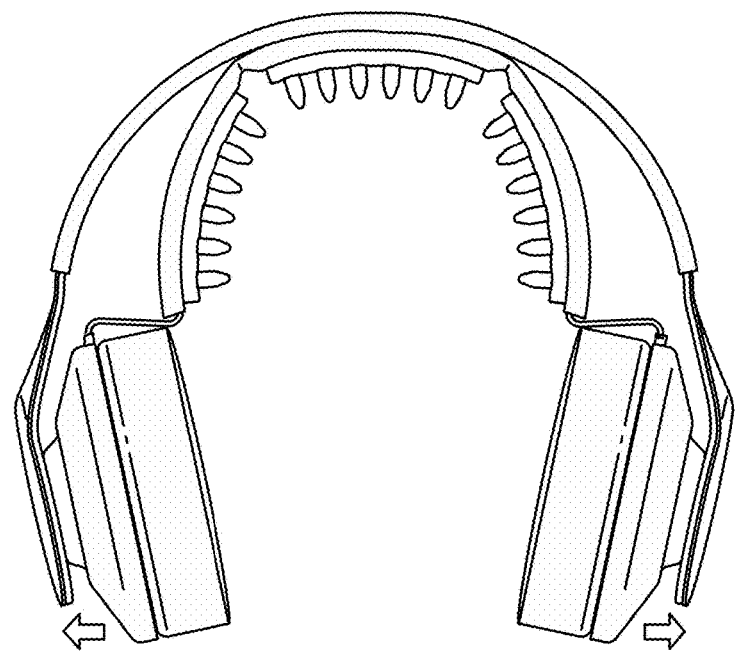
Figure 6D:
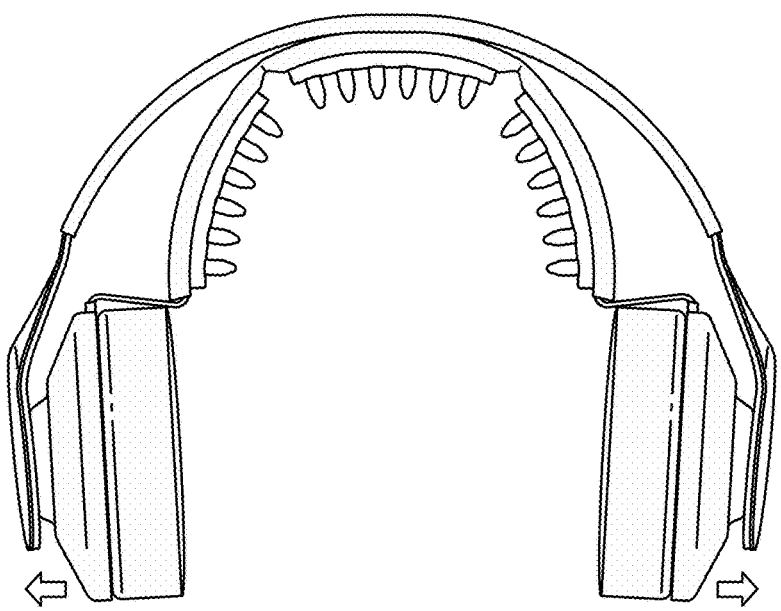

In more detail, as shown in FIGS. 5A-5H, which depict views and aspects of the first specific example, the bridge 130 can have three bridge segments separated from each other by hinged regions, wherein the bridge 130 has an arc length of approximately 70 mm and a radius of curvature of 87 mm, as shown in FIG. 5A. The additional bend angle at two bridge segments between joints of the bridge is approximately 10 degrees, and the bridge 130 has an approximate lateral elastic constant of 12N/cm when force is applied and measured at an end region of the bridge. As shown in FIG. 5B, the radius of curvature of the band 120 (at rest) is 78 mm, and the band 120 has an approximate lateral elastic constant of 1N/cm (when force is applied and measured at a central region of one of the ear pad modules). In the specific example, an overmolded flex cable that functions as a structural link 150 has an approximate lateral elastic constant of 3N/cm when force is applied and measured at the tip of the flex cable, extended out 5 cm. In the specific example, the overmolded flex cable has a length of 53 mm between an end of the bridge 130 and a corresponding one of the set of earpad modules 110 when the earpad module is fully extended. In the specific example, the yaw angle is 1.5 degrees and the roll angle is 18 degrees, as shown in FIGS. 5C and 5D, respectively, and the length of a holder of the ear pad module 110 is ~135 mm from the top of the band 120 to a central region of the earpad (when at the lowest portion of the adjustment range of the earpad), as shown in FIG. 5E, wherein the holder has an adjustment range of 48 mm, as shown in FIG. 5F. In the specific example, the angular ball-and-socket range of motion of an ear pad module 110 in the roll direction is +/−10°, as shown in FIG. 5G, and the angular ball-and-socket range of motion in the yaw direction is +/−10°, as shown in FIG. 5H. In a variation of this example, the angular range of motion of a pad module 110 in the roll direction is +5°/−0.5°, (i.e. 5° deviation from the neutral position in the direction that causes the top of the ear pad module 110 to move away from the contralateral ear pad module 110) in "positive camber", and 0.5° deviation from the neutral position in the direction that causes the top of the ear pad module 110 to move toward the contralateral ear pad module 110 (i.e., "negative camber").

In variations of the first specific example, the bridge 130 can have three bridge segments separated from each other by hinged regions, wherein the bridge 130 has an arc length 50-90 mm and a radius of curvature from 60-100 mm. The additional bend angle at two bridge segments can be from 5-15°, and the bridge 130 can have an approximate lateral elastic constant from 5-20N/cm (when force is applied and measured at a tip region of the bridge). The radius of curvature of the band 120 (at rest) is can be from 65-95 mm, and the band 120 can have an approximate lateral elastic constant from 0.2-5 N/cm (when force is applied and measured at a central region of one of the ear pad modules). In the variations of the first specific example, an overmolded flex cable that functions as a structural link 150 can have an approximate lateral elastic constant from 0.5-10 N/cm when force is applied and measured at the tip of the flex cable, extended out to a usable length during use). The overmolded flex cable can have a length of from 30-70 mm between an end of the bridge 130 and a corresponding one of the set of earpad modules 110 when the earpad module is fully extended. In the variations of the first specific example, the yaw angle can be from 0.2-3 degrees and the roll angle can be from 12-30 degrees, respectively, and the length of a holder of the ear pad module 110 can be from 110-160 mm from the top of the band 120 to a central region of the earpad (when at the lowest portion of the adjustment range of the earpad), wherein the holder can have an adjustment range from 35-65 mm. In the variations of the first specific example, the angular ball-and-socket range of motion of an ear pad module 110 in the roll direction can be from +/−5° to +/−15°, and the angular ball-and-socket range of motion in the yaw direction can be from +/−5° to +/−15°.

An alternative variation of the specific example, as shown in FIGS. 6A-6D, each of the set of links 150 has a substantially low stiffness value (e.g., in terms of elastic modulus) that produces non-axial deflection or buckling in response to outward displacement of the set of ear pad modules 110. However, variations of the specific examples can be configured in any other suitable manner.

1.5 System—Alternative Examples

Figure 7:
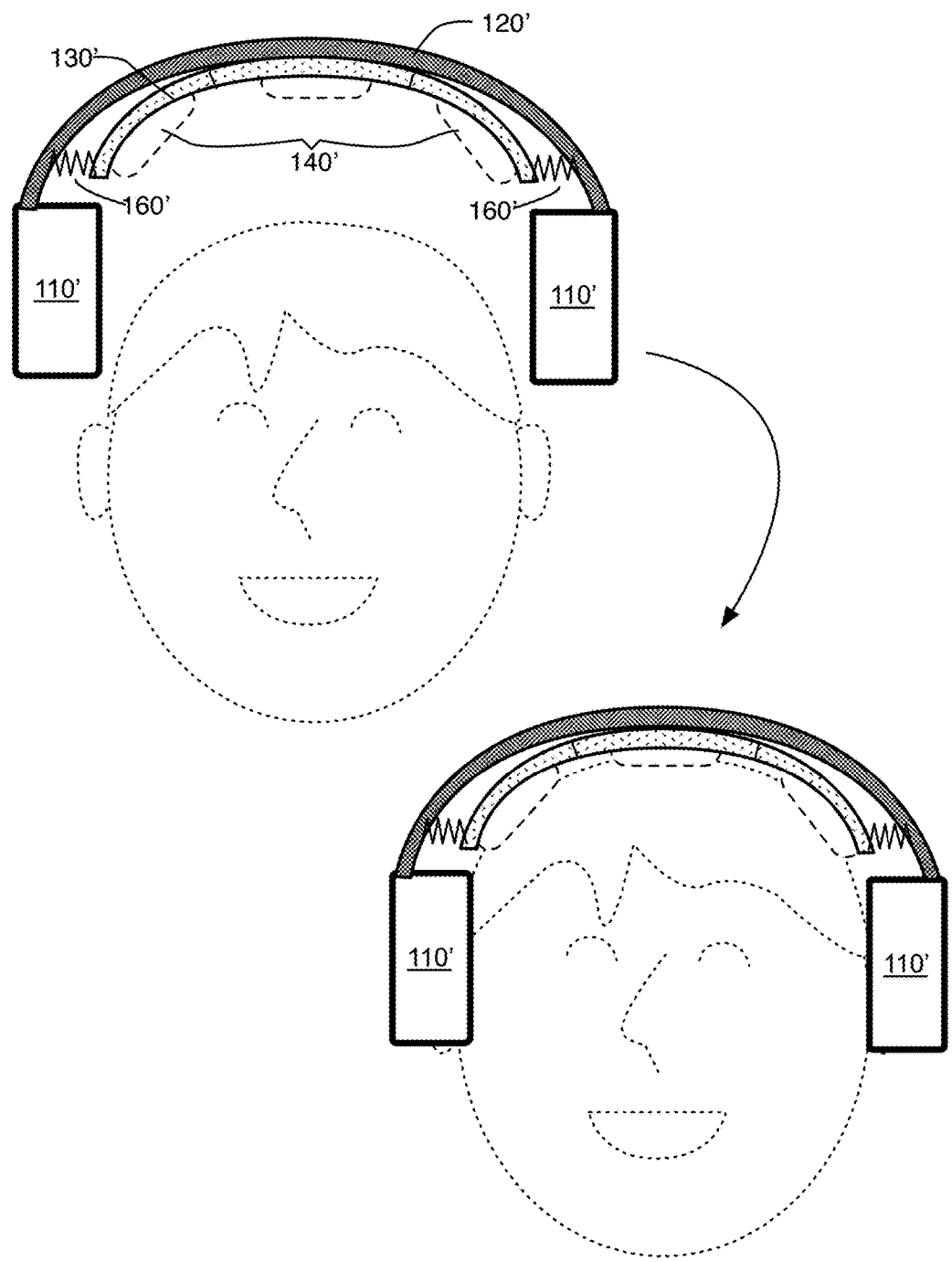
FIG. 7 depicts a first specific alternative example of an embodiment of an electrode positioning system.

In a first specific alternative example, as shown in FIG. 7, the band 120' and the bridge can be directly coupled to each other (e.g., at midregions of the band 120 and the bridge), and/or can be directly coupled to each other at lateral regions by way of elastically deformable and resilient lateral members 160' situated between the band 120' and the bridge 130'. In the first specific alternative example, the lateral members 160' can comprise materials and/or morphologies that result in a desired spring constant, such that outward deflection of lateral portions of the band 120' produces a desired level of outward deflection of lateral portions of the bridge 130' that couple to the set of lateral electrodes 140'. In the first specific example, the bridge 130' can include a set of hinges 135', as described above and shown in at least FIG. 4; however, variations of the first specific alternative example may omit a set of hinges 135' within the bridge 130'. Furthermore, variations of the first specific alternative example can omit direct coupling between the band 120' and the bridge 130'.

Figure 8:
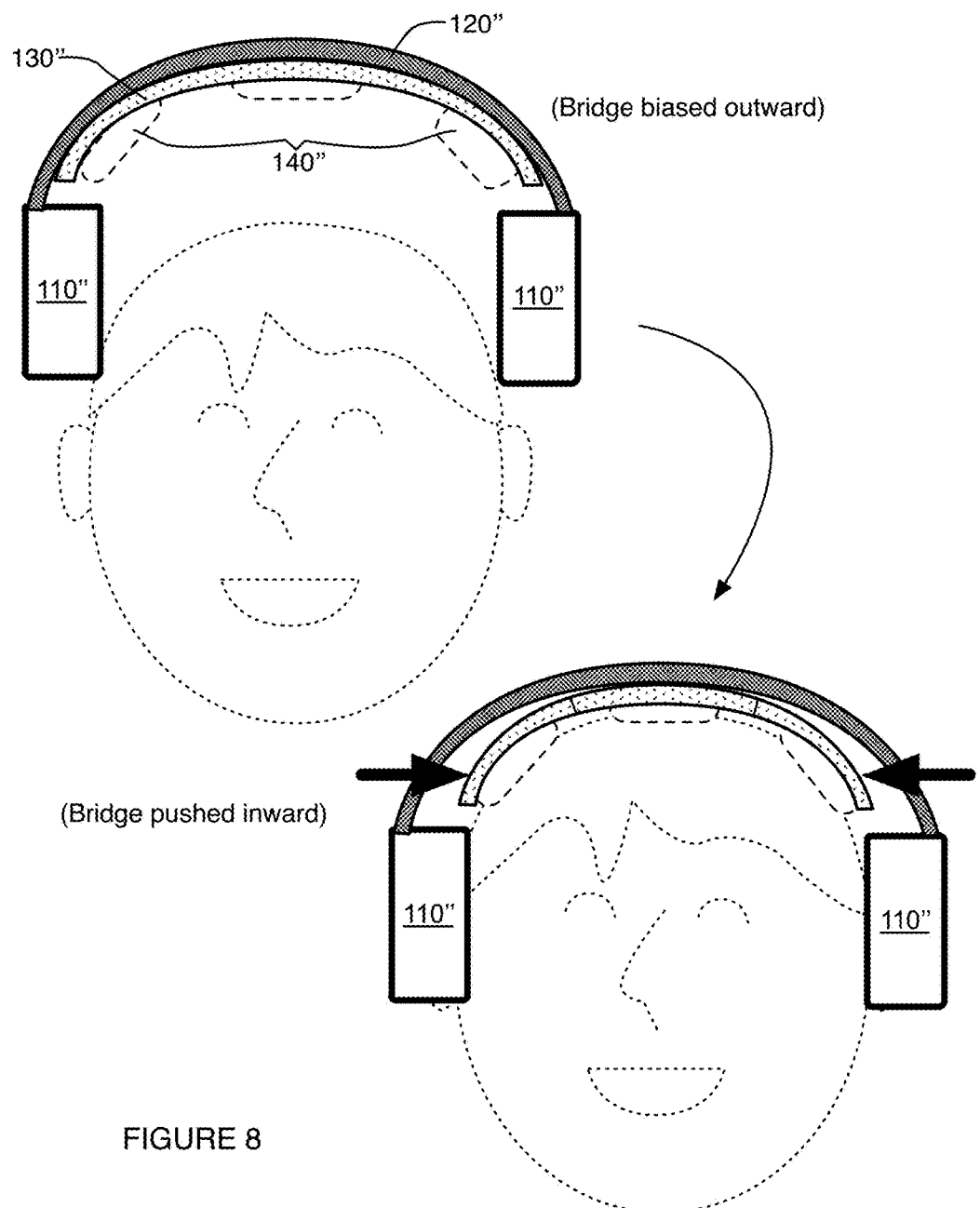
FIG. 8 depicts a second specific alternative example of an embodiment of an electrode positioning system.

In a second specific alternative example, as shown in FIG. 8, lateral regions (e.g. lateral arms) of the bridge 130" can be biased outward toward the band, such that the radius of curvature of the bridge 130" approaches that, or is slightly smaller than that of the band 120". Thus, as the user dons the system 100", and the ear pad modules 110" are pulled apart by the user to accomplish the action of donning the system 100, lateral electrodes housed within the bridge 130" are inherently situated away from the scalp of the user, such that the donning of the system 100" cannot induce shear within each protrusion of the set of lateral electrodes 140" that would otherwise bend flexible protrusions into undesired orientations (e.g., orientations that prevent the protrusions from penetrating hair of the user). Then, once the system 100 is in place at the user's head, the lateral regions (e.g., lateral arms) of the bridge 130" with coupled electrodes can be displaced in a medial direction to position the set of lateral electrodes at the head of the user. In variations of the second specific example the lateral arms of the bridge 130 can be pushed or pulled in the medial direction by one or more of: set screws, magnetic elements, pins, wedges configured to be positioned between the bridge 130 and the band 120, and any other suitable elements.

Figure 9:
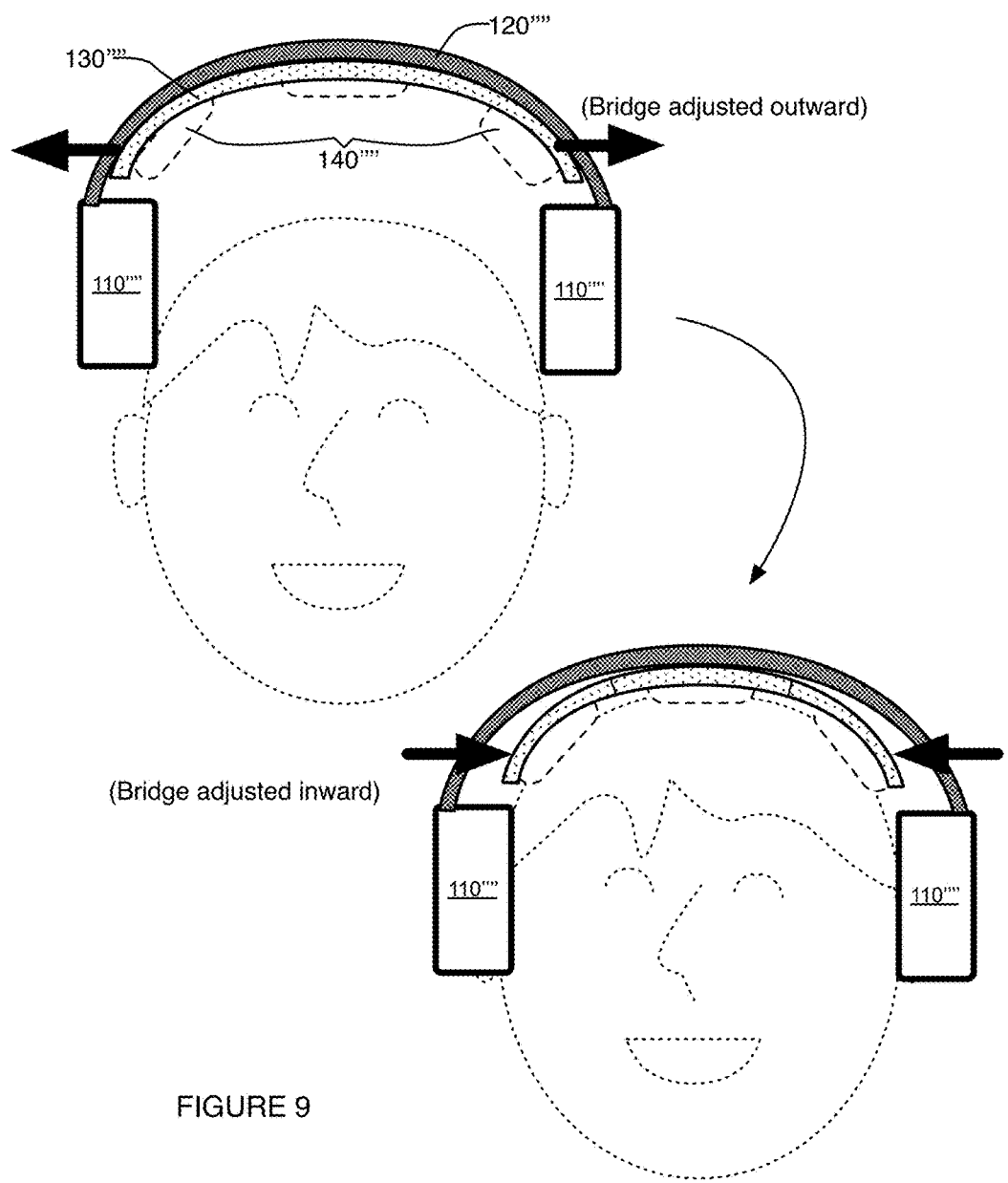
FIG. 9 depicts a third specific alternative example of an embodiment of an electrode positioning system.

In a third specific alternative example, as shown in FIG. 9, lateral regions (e.g., lateral arms) of the bridge 130' may not be biased in any direction, but can be configured such that the characteristic radius of curvature of the bridge 130' can be readily adjusted. In a first mode of operation, as the user prepares to don the system 100', the lateral regions of the bridge 130' can be adjusted outward, which displaces lateral electrodes housed within the bridge 130' away from the scalp of the user, such that the donning of the system 100 cannot induce shear within each protrusion of the set of lateral electrodes 140' that would otherwise bend flexible protrusions into undesired orientations (e.g., orientations that prevent the protrusions from penetrating hair of the user). Then, once the system 100 is in place at the user's head, the lateral regions (e.g., lateral arms) of the bridge 130' with coupled electrodes can be displaced in a medial direction to position the set of lateral electrodes at the head of the user. In the specific example, the lateral arms of the bridge 130''' can be pushed or pulled in the medial direction by one or more of: set screws, magnetic elements, pins, wedges configured to be positioned between the bridge 130''' and the band 120''', and any other suitable elements. Furthermore, in relation to this alternative specific example, transitioning between the different modes of operation can be implemented manually (e.g., by user action) and/or in an automated manner (e.g., using actuators coupled to controllers, etc.).

In a variation of the third specific example, the bridge can comprise a shape memory material (e.g., nitinol, shape-memory polymer, etc.) that can be transitioned between different morphological configurations, upon being subject to different temperatures, or different applied electrical currents. As such, In a first mode of operation, as the user prepares to don the system 100''', the lateral regions of the bridge 130''' can be in an adjusted outward state (i.e., expanded state) using a first heat state and/or a first electric current state, which results in lateral electrodes housed within the bridge 130''' being displaced away from the scalp of the user, and such that the donning of the system 100 cannot induce shear within each protrusion of the set of lateral electrodes 140''' that would otherwise bend flexible protrusions into undesired orientations (e.g., orientations that prevent the protrusions from penetrating hair of the user). Then, once the system 100 is in place at the user's head, the lateral regions (e.g., lateral arms) of the bridge 130''' with coupled electrodes can be displaced in a medial direction to position the set of lateral electrodes at the head of the user (e.g., with a second heat state, with a second electric current state, etc.). In the specific example, the shape memory portion of the bridge 130'''' can thus be coupled to one or more of: a heating element (e.g., resistance heater, Peltier heater, etc.) with a controller, a cooling element (e.g., fan, Peltier cooler, etc.) with a controller, a current source with a controller, and any other suitable component that facilitates transitioning of the shape memory material between different states.

Furthermore, in relation to the third specific alternative examples, transitioning between different states in the bridge 130 can be implemented automatically using sensors integrated with one or more elements of the system 100. For instance, variations of the specific examples can include one or more force sensors, one or more position sensors, and/or any other suitable sensor(s) coupled to one or more of: the links 150, the electrodes 140, bridge 130, the band 120, and the pad module(s) 110 can be configured to sense outward and/or inward deflection of the system in association with donning of the system 100, in order to properly transition the electrodes 140 between outwardly deflected states and inwardly positioned states. Additionally or alternatively, the sensor(s) can be configured to sense changes in position of the system 100 (e.g., picking up of the system, positioning of the system, etc.) using an accelerometer or gyroscope, in order to affect transitioning between different states.

Figure 10:
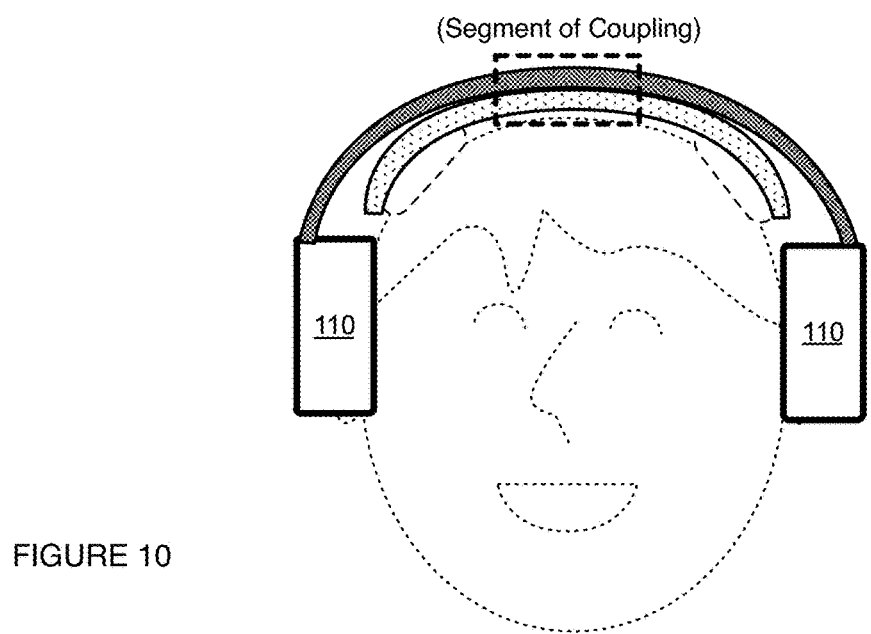
FIG. 10 depicts a fourth specific alternative example of an embodiment of an electrode positioning system.

As shown in FIG. 10, in a fourth specific alternative example that provides partial coupling between the bridge 130 and the band 120, the bridge 130 can be coupled to the band not only at a single point at a vertex region of the bridge 130, but along a segment of the bridge 130. The segment of the bridge 130 can be centered at the vertex region of the bridge 130, but can alternatively be centered about any other suitable point of reference. As such, coupling between the bridge 130 and the band 120 along a length of the bridge 130, where both the bridge 130 and the band 120 are elastically deformable during use of the system 100, will allow expansion of the band 120 to induce some expansion of the bridge 130 in providing a partial coupling mechanism.

The system 100 can, however, comprise any other suitable element(s) or combination of elements that enable displacement of a user's hair and/or enhance coupling between the electrode system 100 and the user. Furthermore, variations of the examples described above can be associated with deflection of the bridge 130 or the band 120 in any other suitable manner.

The system 100 and method of the preferred embodiment and variations thereof can be embodied and/or implemented at least in part as a machine configured to receive a computer-readable medium storing computer-readable instructions. The instructions are preferably executed by computer-executable components preferably integrated with the system 100 and one or more portions of the processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in a flowchart or block diagram may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals or neurostimulation will recognize from the previous detailed description and from the figures and claims, modifications and changes can be made to the preferred embodiments of the invention without departing from the scope of this invention defined in the following claims.

We claim:

1. A system for transcranially stimulating a user and operable at a head region of the user, the system comprising:
    a pair of pad units configured to be positioned at opposing head regions of the user during use of the system, wherein each of the pair of pad units comprises a rigid outer housing;
    a band having a first end coupled to a first pad of the pair of pad units and a second end coupled to a second pad of the pair of pad units, wherein a portion of the band couples to a first region of the rigid outer housing;
    a bridge selectively couplable to an electrode; and
    a pair of links coupled to the pair of pad units, each of the pair of links coupled to the bridge, wherein a portion of a link of the pair of links couples to a second region of the rigid outer housing, interior to the first region of the rigid outer housing, and having an elastic modulus above a threshold modulus such that:
        in a first operation mode, lateral displacement of the pair of pads produces lateral displacement of the electrode away from the head region of the user, and
        in a second operation mode, release of the pair of pads orients protrusions of the electrode approximately normal to the head region of the user.

2. The system of claim 1, wherein each of the pair of pads comprises a compliant portion configured to be positioned circumaurally during operation, and wherein the compliant portion comprises an acoustically transparent material.

3. The system of claim 1, wherein the bridge is coupled to an inferior midregion of the band.

4. The system of claim 3, wherein each of the pair of links is coupled at a second portion of the link to the bridge.

5. The system of claim 1, wherein the bridge is coupled to the band by the pair of links, wherein the pair of links comprise an elastically deformable element configured between the bridge and the band at lateral regions of the bridge and the band.

6. The system of claim 1, wherein the bridge comprises a set of joints and supports a set of electrodes including the electrode during operation, each joint of the set of joints positioned between two adjacent electrode positions corresponding to the set of electrodes.

7. The system of claim 1, wherein the electrode has an array of protrusions supporting an array of permeable bodies, oriented away from the bridge, that facilitate electrical coupling between the system and the head region of the user during use.

8. The system of claim 1, wherein, during operation, relative displacement between the pair of pad units and the band modulates an exposed length of each of the pair of links.

9. The system of claim 8, wherein each of the pair of links comprises a flexible printed circuit within an insulating sheath.

10. The system of claim 1, further including a second electrode unit coupled, by way of a cable, to at least one of the bridge, the band, and a pad unit of the pair of pad units, wherein the second electrode unit is configured to facilitate stimulation of at least one of a frontal cortex region and a prefrontal cortex region of the user during operation.

11. The system of claim 1, wherein the bridge comprises a set of recesses configured to receive a set of electrodes including the electrode, and wherein each of the set of recesses provides an electromechanical connection to an electronics system that facilitates provision of transcranial stimulation to the user.

12. The system of claim 11, wherein the set of recesses supports a pair of lateral electrodes and a middle electrode positioned midway between the pair of lateral electrodes, and wherein the system is configured to transcranially stimulate at least one of a motor cortex region and a premotor cortex region of the user during operation, by way of the set of electrodes.

13. A system for transcranially stimulating a user and operable at a head region of the user, the system comprising:
    a set of ear pad modules providing a pair of anchoring points at contralateral head regions of the user during use of the system, wherein each of the set of ear pad modules comprises a rigid outer housing;
    a band having a first end coupled to a first ear pad module of the set of ear pad modules and a second end coupled to a second ear pad module of the set of ear pad modules, wherein a portion of the band couples to a first region of the rigid outer housing;

a bridge coupled to an inferior midregion of the band and coupleable to a set of electrodes during use of the system, wherein at least one of the set of electrodes has an array of protrusions supporting an array of permeable bodies, oriented away from the bridge, that facilitate electrical coupling between the system and the head region of the user during use; and a set of structural links providing paths for transmitting electrical current to the set of electrodes, the set of structural links coupled to the set of ear pad modules and to the bridge, wherein a portion of a structural link of the set of structural links couples to a second region of the rigid outer housing interior to the first region, and having an elastic modulus above a threshold modulus such that:

in a first operation mode, lateral displacement of the set of ear pad modules produces lateral displacement of the set of electrodes away from the head region of the user, and in a second operation mode, release of the set of ear pad modules orients the array of permeable bodies of the set of electrodes normal to the head region of the user.

14. The system of claim 13, wherein each of the set of ear pad modules comprises a medially-oriented compliant portion comprising an acoustically transparent material.

15. The system of claim 13, wherein the bridge comprises a set of joints, each joint of the set of joints positioned between two adjacent electrode positions corresponding to the set of electrodes.

16. The system of claim 13, wherein each of the set of structural links comprises a flexible printed circuit within an insulating sheath.

17. The system of claim 13, wherein, during operation, relative displacement between the set of ear pad modules and the band modulates an exposed length of each of the set of structural links.

18. The system of claim 13, further comprising a position sensor coupled to at least one of the bridge, the band, and the set of ear pad modules, that senses at least one of the first operation mode and the second operation mode.

* * * * *